US007973050B2

(12) United States Patent
Guiles et al.

(10) Patent No.: US 7,973,050 B2
(45) Date of Patent: *Jul. 5, 2011

(54) ENANTIOMERIC COMPOUNDS WITH ANTIBACTERIAL ACTIVITY

(75) Inventors: Joseph Guiles, Lafayette, CO (US);
Xicheng Sun, Superior, CO (US);
Nebojsa Janjic, Boulder, CO (US);
Sarah Strong, Louisville, CO (US);
Albert Charles Gyorkos, Westminster, CO (US)

(73) Assignee: Crestone, Inc., Boulder, CO (US)

( * ) Notice: Subject to any disclaimer, the term of this patent is extended or adjusted under 35 U.S.C. 154(b) by 727 days.

This patent is subject to a terminal disclaimer.

(21) Appl. No.: 11/853,477

(22) Filed: Sep. 11, 2007

(65) Prior Publication Data
US 2008/0108651 A1 May 8, 2008

Related U.S. Application Data

(60) Provisional application No. 60/826,940, filed on Sep. 26, 2006.

(51) Int. Cl.
A01N 43/42 (2006.01)
A61K 31/44 (2006.01)
A61K 31/47 (2006.01)
C07D 491/02 (2006.01)
C07D 498/02 (2006.01)
C07D 471/02 (2006.01)
C07D 513/02 (2006.01)
C07D 515/02 (2006.01)
C07D 215/00 (2006.01)

(52) U.S. Cl. ........ 514/301; 514/312; 514/310; 546/114; 546/153

(58) Field of Classification Search .................. 514/301, 514/312, 310; 546/114, 153
See application file for complete search history.

(56) References Cited

U.S. PATENT DOCUMENTS

| 4,710,506 | A | 12/1987 | Davies et al. |
| 6,943,175 | B2 | 9/2005 | Berge et al. |
| 7,030,137 | B2 | 4/2006 | Berge et al. |
| 7,220,757 | B2 | 5/2007 | Berge et al. |
| 2008/0146609 | A1 | 6/2008 | Guiles et al. |
| 2008/0227808 | A1 | 9/2008 | Guiles et al. |
| 2009/0163536 | A1 | 6/2009 | Guiles et al. |

FOREIGN PATENT DOCUMENTS

| EP | 0785268 | 7/1997 |
| WO | WO 99/55677 | 11/1999 |
| WO | WO 00/21949 | 4/2000 |
| WO | WO 00/71524 | * 11/2000 |
| WO | WO 2004/052288 | 6/2004 |
| WO | WO 2004/069196 | 8/2004 |
| WO | WO 2004/078119 | 9/2004 |
| WO | WO 2008/039639 | 4/2008 |
| WO | WO 2008/039640 | 4/2008 |
| WO | WO 2008/039641 | 4/2008 |
| WO | WO 2008/039642 | 4/2008 |

OTHER PUBLICATIONS

Kim et al. (Bioorganic & Medicinal Chemistry (2003), 11(24), 5325-5331).*
Lin et al. (Principles and Applications of Asymmetric Synthesis, Wiley Interscience, 2001, p. 1-14).*
U.S. Appl. No. 11/853,314, filed Sep. 11, 2007, Guiles, et al.
Barlett & Perl, N. Engl.J. Med., 353:2503-2505 (2005).
Clabots et al., J. Infect. Dis. 166:561-567 (1992).
Fleischmann et al., Science 269:496-512 (1995).
Jarvest, Bioorg. & Med. Chem. Lett. 14 3937-3941 (2004.
McFarland et al., N. Engl. J. Med. 320:204-210 (1989).
Smith M.B., March J, March's Advanced Org. Chem., 5th ed., Wiley-Interscience, NY, p. 139-143 (2001).
Barker (1995) "An Easy Synthesis of 3-Amino- and 3-Nitrothiophene" Synthetic Comm 25:3729-3734.
Brown et al (2003) "Horizontal Transfer of Drug-Resistant Aminoacyl-Transfer-RNA Synthesis of Anthrax and Gram-Positive Pathogens" EMBO Reports 4(7):692-698.
Elsayed and Zhang (2004) "Bacteremia Caused by Clostrididum symbiosum" J. Clin. Microbiology 42(9):4390-4392.
Hurdle et al (2005) "Prospects for Aminoacyl-tRNA Synthetase Inhibitors as New Antimicrobial Agents" Antimicrobial Agents and Chemotherapy 49(12):4821-4833.
Jarvest et al (2003) "Conformational Restriction of Methionyl tRNA Synthetase Inhibitors Leading to Analogues with Potent Inhibition and Excellent Gram-Positive Antibacterial Activity" Bioorganic & Medicinal Chemistry Letters 13:1265-1268.
Jiang et al (2009) "Clostridium glycolicum Wound Infections: Case Reports and Review of the Literature" J. Clin. Microbiology 47(5):1599-1601.
King (1994) "Bioisosteres, Conformational Restriction, and Prodrugs—Case History: An Example of a Conformational Restriction Approach" Medicinal Chemistry: Principle and Practice:206-225.
Office Action mailed Nov. 24, 2010 with respect to U.S. Appl. No. 11/853,636.
Office Action mailed Sep. 15, 2010 with respect to U.S. Appl. No. 11/853,314.
Office Action mailed Sep. 15, 2010 with respect to U.S. Appl. No. 11/853,589.
Smith-Slatas et al (Mar. 27, 2006) "Clostridium septicum Infections in Children: A Case Report and Review of the Literature" Pediatrics 117:e796-e805 (http:www.pediatrics.org/cgi/content/full/117/4/e796).

(Continued)

Primary Examiner — Shengjun Wang
Assistant Examiner — Uma Ramachandran
(74) Attorney, Agent, or Firm — Swanson & Bratschun, L.L.C.

(57) ABSTRACT

Novel compounds in enantiomeric excess that are inhibitors of bacterial methionyl synthetase (MetRS) are disclosed. Also disclosed are methods for their preparation and their use in therapy as antibacterial agents, and in particular their use in therapy for Clostridium difficile infection.

9 Claims, No Drawings

OTHER PUBLICATIONS

Gentry et al (2003) "Variable Sensitivity to Bacterial Methionyl-tRNA Synthetase inhibitors Reveals Subpopulations of *Streptococcus pneumoniae* with Two Distinct methionyl-tRNA Synthetase Genes" Antimicrobial Agents and Chemotherapy 47(6):1784-1789.

Jarvest et al (2002) "Nanomolar Inhibitors of *Staphylococcus aureus* Methionyl tRNA Synthetase with Potent Antibacterial Activity Against Gram-Positive Pathogens" Journal of Medicinal Chemistry 45(10):1959-1962.

EP Supplemental Search Report (Mar. 21, 2011) received in EP Application No. 07842226.8.

Bartlett et al (1978) "Role of *Clostridium difficile* in Antibiotic-Associated Pseudomembranous colitis" Gastroenterology 75(5):778-782.

Critchley et al (2005) "Antibacterial Activity of REP8839, a New Antibiotic for Topical Use" Antimicrobial Agents and Chemotherapy 49(10):4247-4252.

Hall and O'Toole (1935) "Intestinal Flora in Newborn Infants with Description of a New Pathogenic Anaerobe" American Journal of Diseases of Children 49:390-402.

Loo et al (2005) "A Predominantly Clonal Multi-Institutional Outbreak of *Clostridium difficile*-Associated Diarrhea with High Morbidity and Mortality" New England Journal of Medicine 353:2442-2449.

Lyerly et al (1988) "*Clostridium difficile*: Its Disease and Toxins" Clinical Microbiology Reviews 1(1):1-18.

Pépin et al (2005) "Increasing Risk of Relapse After Treatment of *Clostridium difficile* Colitis in Quebec, Canada" Clin. Infect. Dis. 40:1591-1597.

Teasley et al (1983) "Prospective Randomised Trial of Metronidazole Versus Vancomycin for *Clostridium-difficile*-Associated Diarrhoea and Colitis" The Lancet 2:1043-104.

Thomas et al (2003) "Antibiotics and Hospital-Acquired *Clostridium difficile*-Associated Diarrhoea: a Systematic Review" Journal of Antimicrobial Chemotherapy 51:1339-135.

Voth and Ballard (2005) "*Clostridium-difficile* Toxins: Mechanism of Action and Role in Disease" Clinical Microbiology Reviews 18(2):247-16.

Wilcox and Spencer (1992) "*Clostridium difficile* Infection: Responses, Relapses and Re-Infections" Journal of Hospital Infection 22:85-92.

* cited by examiner

SEQUENCE LISTING

```
<160> NUMBER OF SEQ ID NOS: 2

<210> SEQ ID NO 1
<211> LENGTH: 33
<212> TYPE: DNA
<213> ORGANISM: Artificial
<220> FEATURE:
<223> OTHER INFORMATION: Primer

<400> SEQUENCE: 1
ctgcagagct agcaaaccga gtttttatgt aac                              33

<210> SEQ ID NO 2
<211> LENGTH: 33
<212> TYPE: DNA
<213> ORGANISM: Artificial
<220> FEATURE:
<223> OTHER INFORMATION: Primer

<400> SEQUENCE: 2
ctttctaagc ttctactaac gaacctcgga tcc                              33
```

ENANTIOMERIC COMPOUNDS WITH ANTIBACTERIAL ACTIVITY

RELATED APPLICATIONS

This application claims the benefit under 35 U.S.C. §119, of U.S. Provisional Patent Application Ser. No. 60/826,940 entitled ENANTIOMERIC COMPOUNDS WITH ANTIBACTERIAL ACTIVITY, filed Sep. 26, 2006, and incorporated by reference herein in its entirety. This application is related to U.S. patent applications: METHODS AND COMPOSITIONS FOR TREATMENT OF CLOSTIDIUM BASED INFECTION, Ser. No. 60/826,957, filed Sep. 26, 2006 and to corresponding US non-provisional and PCT applications filed on Sep. 11, 2007; SUBSTITUTED THIENOPYRIDONE COMPOUNDS WITH ANTIBACTERIAL ACTIVITY, Ser. No. 60/826,945 filed Sep. 26, 2006 and corresponding US non-provisional and PCT applications filed on Sep. 11, 2007; and SUBSTITUTED PHENYLETHER-THIENOPYRIDONE COMPOUNDS WITH ANTIBACTERIAL ACTIVITY, Ser. No. 60/826,954 filed Sep. 26, 2006 and corresponding US non-provisional and PCT applications filed on Sep. 11, 2007. The current application is also related to U.S. Pat. No. 6,943,175, filed Dec. 5, 2003, U.S. Pat. No. 7,030,137, filed Feb. 27, 2004, and to U.S. patent application Ser. No. 10/729,416, filed Dec. 5, 2003 and Ser. No. 11/223,327, filed Sep. 9, 2005. Each of the above referenced applications and patents are incorporated by reference herein for all purposes.

TECHNICAL FIELD

The present invention relates to novel enantiomers of bicyclic heteroaromatic compounds that inhibit bacterial methionyl tRNA synthetases (MetRS) and to processes for their preparation and their use in therapy as antibacterial agents. In addition, the present invention relates to the use of these enantiomeric compounds in the treatment of *Clostridium difficile* based infection and disease.

BACKGROUND OF THE INVENTION

The search for antibacterial agents began in the late 1800s with the realization that "germs" caused human disease. Over the past century scientists have developed a variety of drugs useful in the targeting and inhibition of numerous bacterial strains. In particular, antibacterial agents known as antibiotics were developed and are in common use throughout the industrialized world to treat most known bacterial infections. Originally, antibiotics like penicillin inhibited replication of bacteria by blocking the action of transpeptidase, an enzyme responsible for the building of bacterial cell walls. However, due to overuse and resistance adaptations of many bacterial strains, many antibiotics have lost some or all of their effectiveness at treating infection. A line of antibacterial agents that target new molecular growth mechanisms would be useful in avoidance of further enhancement of antibiotic resistance. One such target is tRNA synthetase.

tRNA synthetases are involved in protein biosynthesis so that inhibition thereof may be expected to lead to a cessation of cell growth. Thus, for instance, the compound mupirocin has been shown to be an inhibitor of the isoleucyl tRNA synthetase. Mupirocin is produced by the organism *Pseudomonas fluorescens*, and is an antibacterial agent used as the active ingredient in the product Bactroban®, marketed by GlaxoSmithKline. Each tRNA synthetase represents a separate target for drug discovery. tRNA synthetase inhibitors which are selective for bacterial cells over mammalian cells are of considerable therapeutic interest as they have the potential to be used as antibacterial agents.

The sequence of the tRNA synthetase genes in the Gram positive organism *S. aureus* have recently been determined (see, for instance, European Patent application no 97300317.1, SmithKline Beecham, for *S. aureus* MetRS), thereby assisting the process of identifying inhibitors. In addition, the sequence of tRNA synthetase genes in other pathogenic bacteria, for instance the Gram negative organism *H. influenzae*, has also been published (R. D. Fleischmann et al., Science, 269, 496-512, 1995).

Several compounds have recently been disclosed for their inhibitory activity toward MetRS and for their capacity as antibacterial agents. In particular, Jarvest et al. described various bicyclic heteroaromatic compounds that have shown some degree of MetRS inhibition including one particular compound that is the enantiomer with R configuration of a left-hand-side tetrahydroquinoline compound (Bioorg. & Med. Chem. Lett. 14 (2004) 3937-3941).

One particularly interesting bacterial target is the organism *Clostridium difficile* (*C. difficile*). *C. difficile* is becoming a more prevalent infectious agent, where one to three percent of healthy individuals are carriers of the organism. (Bartlett & Perl, N. Engl. J Med., 353, 2503-2505, 2005; Clabots et al., J Infect. Dis., 166, 561-567, 1992; McFarland et al., N. Engl. J Med., 320, 204-210, 1989). The risk of infection and disease becomes increasingly prevalent in the immunodeficient, elderly, and especially, elderly in healthcare settings, e.g., nursing home, hospital, doctors office, etc. Few conventional antibacterial drugs have shown promise in the treatment of *C. difficile*, in fact only vancomycin is approved by the FDA for treatment of *C. difficile* associated diarrhea (CDAD). As such, there is a need in the art to obtain additional approaches to the treatment of *C. difficile* based infection, especially treatments that avoid conventional antibiotic treatments and therefore antibiotic resistance.

Against this backdrop the present invention has been discovered.

DETAILED DESCRIPTION OF THE INVENTION

The invention provides novel compounds that are potent inhibitors of bacterial methionyl tRNA synthetase (MetRS). The compounds of the invention are shown to have broad applicability as antibacterial agents for numerous Gram-positive and Gram-negative bacteria. MetRS inhibitors have best activity against Gram-positive organisms and far weaker activity against Gram-negative organisms. In particular, the compounds of the invention are shown to have surprisingly potent antibacterial activity against *C. difficile*.

Compounds of the invention are novel bicyclic heteroaromatic enantiomers which show unexpected and potent inhibition of bacterial MetRS. These compounds show little or no inhibition of mammalian MetRS. The compounds of the invention are for use in therapy as antibacterial agents. In particular, compounds of the invention have shown surprisingly strong potency against Gram-positive bacteria and in particular *C. difficile*.

The invention provides compounds of the formula (I):

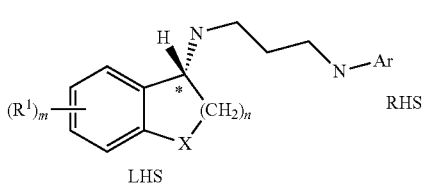

in which:

Ar is the right hand side (RHS) substituent and has a substituted or unsubstituted aryl or heteroaryl group;

X is selected from the group consisting of NH, O, S, SO, $SO_2$, or $CH_2$;

n is 1, 2 or 3;

* indicates an asymmetric carbon atom, wherein when n is 2 or 3, then * is R configuration; wherein when n is 1 and X is $CH_2$, then * is R configuration; and wherein when n is 1 and X is selected from the group consisting of NH, O, S, SO, or $SO_2$, then * is S configuration.

m is 0, 1, 2, 3, or 4; and $R^1$ is independently selected from halo, cyano, hydroxyl, $(C_{1-6})$alkyl (optionally substituted by halo, hydroxyl, amino, carboxy, or $(C_{1-6})$alkoxycarbonyl), $(C_{3-7})$cycloalkyl, $C_{(1-6)}$alkoxy, amino, mono- or di-$(C_{1-6})$alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl and heterocyclic.

Preferred embodiments of the invention are those compounds of the formula (IIa) and (IIb):

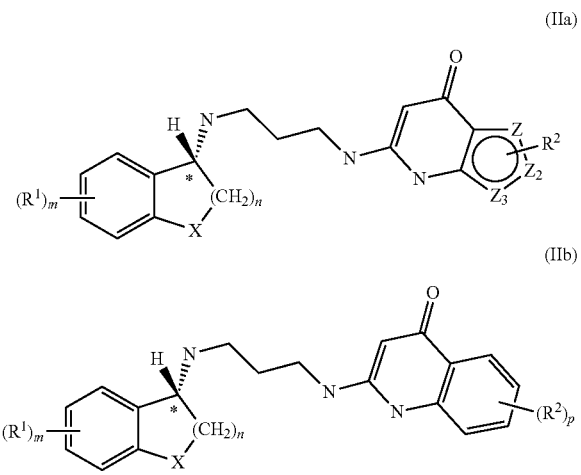

in which:

X is selected from the group consisting of NH, O, S, SO, $SO_2$, or $CH_2$;

n is 1, 2 or 3;

* indicates an asymmetric carbon atom, wherein when n is 2 or 3, then * is R configuration; wherein when n is 1 and X is $CH_2$, then * is R configuration; and wherein when n is 1 and X is selected from the group consisting of NH, O, S, SO, or $SO_2$, then * is S configuration;

$R^1$ is independently selected from halo, cyano, hydroxyl, $(C_{1-6})$alkyl (optionally substituted by halo, hydroxyl, amino, carboxy, or $(C_{1-6})$alkoxycarbonyl), $(C_{3-7})$cycloalkyl, $C_{(1-6)}$ alkoxy, amino, mono- or di-$(C_{1-6})$alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl and heterocyclic;

m is 0, 1, 2, 3 or 4;

p is 0, 1, 2 or 3;

$R^2$ is independently selected from halo, cyano, hydroxyl, $(C_{1-6})$alkyl (optionally substituted by halo, hydroxyl, amino, carboxy, or $(C_{1-6})$alkoxycarbonyl), $(C_{3-7})$cycloalkyl, $C_{(1-6)}$ alkoxy, amino, mono- or di-$(C_{1-6})$alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl and heterocyclic; and when $Z_1$ is S, $Z_2$ and $Z_3$ are CH; when $Z_2$ is S, $Z_1$ and $Z_3$ are CH; and when $Z_3$ is S, $Z_1$ and $Z_2$ are CH.

Compounds of formula (IIa) and (IIb) are chiral non-racemic and are isolable in high enantiomeric excess in either their R or S configurations. In some embodiments, the compounds of formula (II) have at least 60% enantiomeric excess of the R-enantiomer or S-enantiomer, and can be enantiomerically pure, where substantially 100% of the compound is a single enantiomer (as measured by optical rotation, chiral HPLC, or as measured on a weight/weight basis). In preferred embodiments the enantiomer compounds of the invention have either an R configuration or an S configuration.

A preferred group of compounds of formula (IIa) and (IIb) are those in which the left-hand-side (LHS) of the formula is as shown in formula (III) and formula (IV) and the right-hand-side (RHS) of the formula (or Ar) is either a thienopyridone group (formula III) or a quinolone group (formula IV):

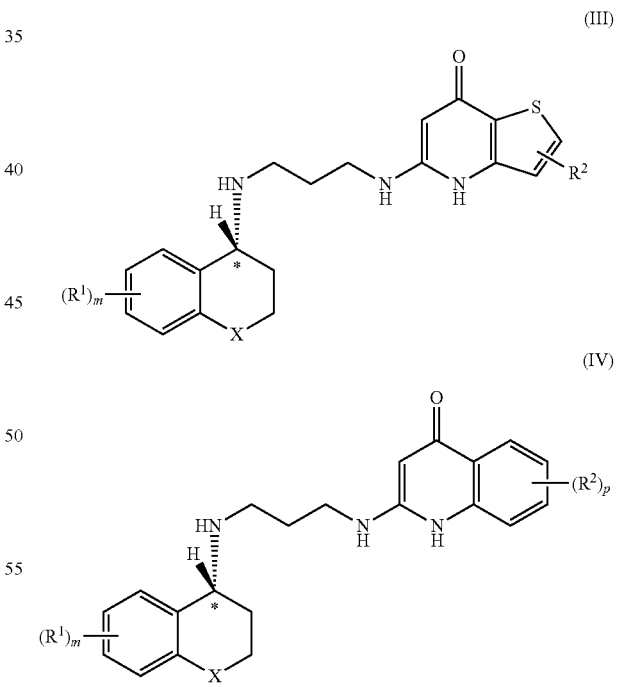

in which:

X is defined as in Formula (IIa) and (IIb).

$R^1$ is defined as in Formula (IIa) and (IIb). In more preferred embodiments, $(R^1)_m$ can be further defined as a 6, 8 substitution on the ring where they can be the same or different substituents, and preferably bromine, chlorine, iodine or sulfane;

m is defined as in Formula (IIa) and (IIb);
R² is defined as in Formula (IIa) and (IIb); and
p is defined as in Formula (IIa) and (IIb).

As above, formulas (III) and (IV) are characterized by an asymmetric carbon atom marked with an asterisk (*). The bonds surrounding this carbon give rise to an R configuration in compounds of formula (III) or (IV). Compounds of formula (III) or (IV) are typically chiral non-racemic and are isolable in high enantiomeric excess of the R enantiomer. In some embodiments, the compounds of either formula (III) or (IV) have at least 60% R enantiomer and can be enantiomerically pure in which substantially 100% of the compound is in the R configuration (as measured by optical rotation, chiral HPLC, or weight). In preferred embodiments the compounds having formula (III) or (IV) are in the R configuration.

Another preferred group of compounds of formula (IIa) and (IIb) are those in which the LHS of the formula is a dihydrobenzofuran group and the RHS of the formula is a thienopyridone group (formula V):

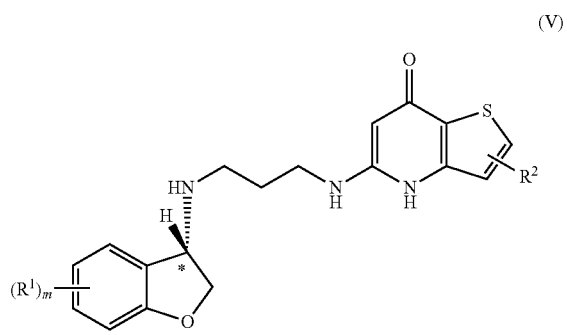

(V)

in which:

R¹ is defined as in formula (IIa) and (IIb). In more preferred embodiments, $(R_1)_m$ can be further defined as a 5, 7 substitution on the ring where they can be the same or different substituents, and preferably bromine, chlorine, iodine or sulfane;

m is defined as in Formula (IIa) and (IIb);
R² is defined as in Formula (IIa) and (IIb); and As above, formula (V) is characterized by an asymmetric carbon atom marked with an asterisk (*). The bonds surrounding this carbon give rise to an S configuration. Compounds of formula (V) are typically chiral non-racemic and are isolable in high enantiomeric excess in the S enantiomer. In some embodiments, the compounds of formula (V) have at least 60% S enantiomer and can be enantiomerically pure in which substantially 100% of the compound is in the S configuration (as measured by optical rotation or weight). In preferred embodiments the compounds having formula (V) are in the S configuration.

Several preferred compounds of the invention include the compounds of examples 1-12. In particular, preferred compounds of the invention include the compounds of formulas VI-XI (shown below and see Table 1):

5-[3-((R)(−)-5,7-Dibromo-1,2,3,4-tetrahydro-naphthalen-1-ylamino)-propylamino]-4H-thieno[3,2-b]pyridine-7-one (formula VI);

5-[3-((R)(+)-8-Bromo-6-chloro-chroman-4-ylamino)-propylamino]-4H-thieno[3,2-b]pyridine-7-one (formula VII);

5-[3-((R)(+)-6,8-Dibromo-1,2,3,4-tetrahydro-quinolin-4-ylamino)-propylamino]-4H-thieno[3,2-b]pyridine-7-one (formula VIII);

5-[3-((R)(+)-6,8-Dibromo-chroman-4-ylamino)-propylamino]-4H-thieno[3,2-b]pyridine-7-one (formula IX);

2-[3-((R)(+)-6,8-Dibromo-chroman-4-ylamino)-propylamino]-1H-quinolin-4-one (formula X);

5-[3-((S)-5,7-Dibromo-benzofuran-3-ylamino)-propylamino]-4H-thieno[3,2-b]pyridine-7-one (formula XI):

-continued

Table 1 provides a summary of the compounds described herein, showing LHS (left hand side) and RHS (right hand side) functionality:

STRUCTURE

| FORM NO./ Ex. NO. | LHS~N(H)~~~N(H)~RHS | LHS (substituted or unsubstituted) | RHS (substituted or unsubstituted) |
|---|---|---|---|
| (IIb) | | Chroman, Tetrahydroquinoline, Dihydrobenzofuran, Tetrahydronaphthalene, or Benzothiopyran | Quinolone |
| (III) | | Chroman, Tetrahydroquinoline, Benzothiopyran, or Tetrahydronaphthalene | Thienopyridone |
| (IV) | | Chroman, Tetrahydroquinoline, Benzothiopyran, or Tetrahydronaphthalene | Quinolone |
| (V) | | Dihydrobenzofuran | Thienopyridone |
| (VI) [Ex. 10] | | 5-[3-((R)(−)-5,7-Dibromo-1,2,3,4-tetrahydro-naphthalen-1-ylamino)-propylamino]-4H-thieno[3,2-b]pyridine-7-one | |

-continued

Table 1 provides a summary of the compounds described herein, showing LHS (left hand side) and RHS (right hand side) functionality:

| FORM NO./ Ex. NO. | STRUCTURE LHS-NH-(CH2)3-NH-RHS | LHS (substituted or unsubstituted) | RHS (substituted or unsubstituted) |
|---|---|---|---|
| (VII) [Ex. 4] | | | 5-[3-((R)(+)-8-Bromo-6-chloro-chroman-4-ylamino)-propylamino]-4H-thieno[3,2-b]pyridine-7-one |
| (VIII) [Ex. 8] | | | 5-[3-((R)(+)-6,8-Dibromo-1,2,3,4-tetrahydro-quinolin-4-ylamino)-propylamino]-4H-thieno[3,2-b]pyridine-7-one |
| (IX) [Ex. 2] | | | 5-[3-((R)(+)-6,8-Dibromo-chroman-4-ylamino)-propylamino]-4H-thieno[3,2-b]pyridine-7-one |
| (X) [Ex. 6] | | | 2-[3-((R)(+)-6,8-Dibromo-chroman-4-ylamino)-propylamino]-1H-quinolin-4-one |

-continued

Table 1 provides a summary of the compounds described herein, showing LHS (left hand side) and RHS (right hand side) functionality:

STRUCTURE

| FORM NO./ Ex. NO. | LHS~N(H)~~~N(H)~RHS | LHS (substituted or unsubstituted) | RHS (substituted or unsubstituted) |
|---|---|---|---|
| (XI) [Ex. 11] | (structure: 5,7-dibromo-2,3-dihydrobenzofuran-3-yl (S) connected via HN–CH$_2$CH$_2$CH$_2$–NH to 4H-thieno[3,2-b]pyridin-7-one) | | 5-[3-((S)-5,7-Dibromo-2,3-dihydro-benzofuran-3-ylamino)-propylamino]-4H-thieno[3,2-b]pyridine-7-one |

Salts may be formed from inorganic and organic acids. Representative examples of suitable inorganic and organic acids from which pharmaceutically acceptable salts of compounds of formulas (I-XI) may be formed include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

When used herein, the term "alkyl" and similar terms such as "alkoxy" to include all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the terms "alkenyl" and "alkynyl" include all straight chain and branched isomers. Representative examples thereof include vinyl, ethynyl and 1-propynyl.

Preferred substituents for alkyl and alkenyl groups include, for example, and unless otherwise defined, halogen, cyano, azido, nitro, carboxy, $(C_{1-6})$alkoxycarbonyl, carbamoyl, mono- or di-$(C_{1-6})$alkylcarbamoyl, sulpho, sulphamoyl, mono- or di-$(C_{1-6})$alkylsulphamoyl, amino, mono- or di-$(C_{1-6})$alkylamino, acylamino, ureido, $(C_{1-6})$alkoxycarbonylamino, 2,2,2-trichloroethoxycarbonylamino, aryl, heterocyclic, hydroxy, $(C_{1-6})$alkoxy, acyloxy, oxo, acyl, 2-thienoyl, $(C_{1-6})$alkylthio, $(C_{1-6})$alkylsulphinyl, $(C_{1-6})$alkylsulphonyl, hydroxyimino, $(C_{1-6})$alkoxyimino, hydrazino, hydrazono, benzohydroximoyl, guanidino, amidino and iminoalkylamino.

When used herein, the term "aryl" includes, unless otherwise defined, phenyl or naphthyl optionally substituted with up to five, preferably up to three, substituents.

When substituted, an aryl group may have up to four substituents. Preferred substituents for an aryl group include, for example, and unless otherwise defined, halogen, cyano, $(C_{1-6})$alkyl, mono to perfluoro$(C_{1-3})$alkyl, $(C_{3-7})$cycloalkyl, $(C_{2-6})$alkenyl, $(C_{1-6})$alkoxy, $(C_{2-6})$alkenoxy, arylC$_{(1-6)}$alkoxy, halo$(C_{1-6})$alkyl, hydroxy, amino, mono- or di-$(C_{1-6})$alkylamino, acylamino, nitro, carboxy, $(C_{1-6})$alkoxycarbonyl, $(C_{1-6})$alkenyloxycarbonyl, $(C_{1-6})$alkoxycarbonyl$(C_{1-6})$alkyl, carboxy$(C_{1-6})$alkyl, $(C_{1-6})$alkylcarbonyloxy, carboxy$(C_{1-6})$alkyloxy, $(C_{1-6})$alkoxycarbonyl$(C_{1-6})$alkoxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl, carbamoyl, mono- and di-$(C_{1-6})$alkylcarbamoyl, and heterocyclic.

When used herein, the term "heteroaryl" includes single or fused rings comprising up to four hetero-atoms in the ring selected from oxygen, nitrogen and sulphur. Preferably the heteroaryl ring comprises from 4 to 7, preferably 5 to 6, ring atoms. A fused heteroaryl ring system may include carbocyclic rings and need only include one heterocyclic ring.

When used herein, the term "heterocyclic" includes aromatic and non-aromatic single or fused rings comprising up to four hetero-atoms in the ring selected from oxygen, nitrogen and sulphur. Suitably the heterocyclic ring comprises from 4 to 7, preferably 5 to 6, ring atoms. A fused heterocyclic ring system may include carbocyclic rings and need only include one heterocyclic ring.

When substituted, a heteroaryl or a heterocyclic group may have up to three substituents. Preferred substituents include those previously mentioned for an aryl group as well as oxo.

When used herein, the terms "halogen" and "halo" include fluorine, chlorine, bromine, and iodine and fluoro, chloro, bromo, and iodo, respectively.

When used herein, the term "enantiomer" refers to one of two compounds that differ in handedness and are said to have an enantiomeric relationship. In order to convert one enantiomer to the other requires breaking and reforming bonds or distorting the molecule through planar geometry. An enantiomer is said to be in enantiomeric excess when one configuration of the enantiomer is present in excess over the other enantiomer configuration. Enantiomeric excess can be measured on the basis of weight/weight or by the net optical rotation of the mixture.

When used herein, the terms "(R)" or "R" and "(S)" or "S" is based on naming conventions well known to one of skill within the art, for example, an R-configuration is based on a compound's actual geometry, typically using the Cahn-Ingold-Prelog priority rules to classify the form (Smith M. B., March, J, March's Advanced Organic Chemistry, 5$^{th}$ ed. Wiley-Interscience, NY, 2001, p 139-141). As has been described herein above, compounds of the invention have been characterized as having R configuration or an S configuration.

The compounds according to the invention are suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. All impure or less pure forms of a compound according to the invention may, for example, be used in the preparation of a more pure form of the same compound or of a related compound (for example a corresponding derivative) suitable for pharmaceutical use.

The compounds of formulas (I)-(XI) may be prepared by methods described herein or by methods described in the prior art that are incorporated by reference herein below.

In one embodiment, an enantiomerically enriched compound of the present invention may be prepared by chiral separation as depicted in process I.

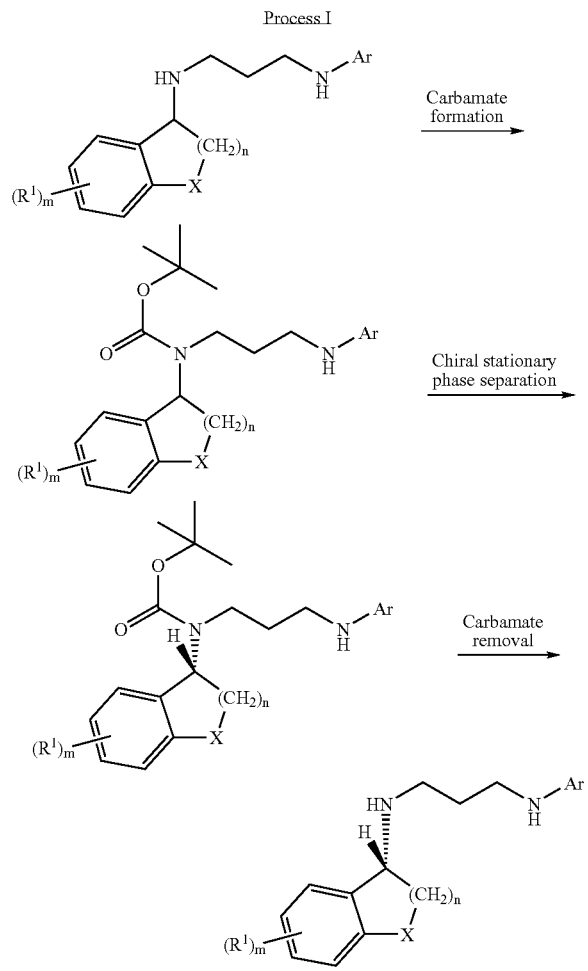

The desired compounds were prepared as racemic mixtures according to methods described in U.S. patent application Ser. No. 11/853,314, entitled "Substituted Thienopyridone Compounds with Antibacterial Activity, filed Sep. 11, 2007. The racemates were then separated via chiral stationary phase chromatography. The racemates were converted to a carbamate functionality such as t-butoxycarbonyl (Boc) as a means to facilitate the chiral separation. The racemic mixture of compounds was Boc-protected under known conditions with sodium hydride and Boc-anhydride in THF (Carbamate formation in process 1). The Boc-protected racemic mixtures were then separated into the single enantiomers by preparative chiral chromatography (prep-HPLC) and the enantiomers were isolated (see Chiral separation in process 1). The separated enantiomers are then deprotected (see Carbamate removal in process 1) to give the final compounds in high enantiomerically enriched form.

In one embodiment, an enantiomerically enriched compound of the present invention may be prepared via catalytic asymmetric synthesis as depicted in process II.

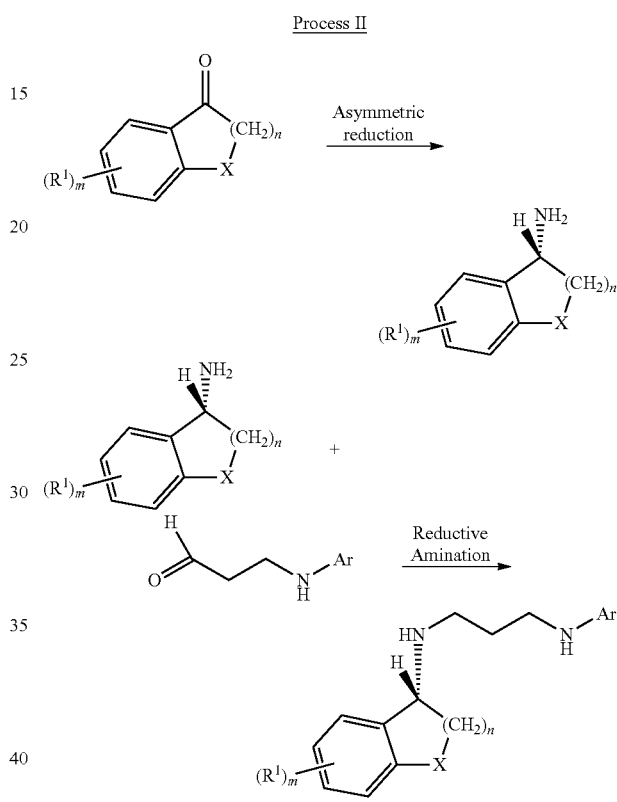

The desired compounds were prepared as enantiomerically enriched forms via a catalytic asymmetric transfer hydrogenation of a ketone to an alcohol followed by conversion to the amine via an intermediate azide. Reductive amination and removal of protecting group gave the final compounds.

The compounds of this invention are active against a range of important pathogenic bacteria, including Gram positive organisms, such as Staphylococci, for instance *S. aureus* Oxford and coagulase negative strains of Staphylococci such as *S. epidermidis*; Streptococci, for instance *S. pyogenes* ATCC19615 and *S. pneumoniae* R6; *Clostridium*, for instance *C. difficile*, and Enterococci, for instance *E. faecalis* 1 and *E. faecium*. Preferably, compounds of this invention are also active against Gram negative organisms, such as *Haemophilus*, for instance *H. influenzae* Q1; *Moraxella*, for instance *M. catarrhalis* 1502; *Helicobacter*, for instance *H. pylori* ATCC700824; and *Escherichia*, for instance *E. Coli* DC0. The most preferred compounds of the present invention will be active against the organisms *C. difficile*, *S. aureus*, *S. pneumoniae*, *E. faecalis*, *E. faecium*, *H. influenzae*, *H. pylori*, and *M. catarrhalis*.

In addition, compounds of this invention are active against Staphylococci organisms such as *S. aureus* and coagulase negative strains of Staphylocci such as *S. epidermidis* which are resistant (including multiply-resistant) to other antibacterial agents, for instance, β-lactam antibiotics such as, for example, methicillin, macrolides, aminoglycosides, oxazolidinones, and lincosamides.

Compounds of the present invention are also active against strains of *E. faecalis* including vancomycin resistant strains and therefore of use in treating infections associated with VRE organisms. Furthermore, compounds of the present invention are useful in the treatment of Staphylococci organisms which are resistant to mupirocin.

Compounds of the present invention are particularly potent, i.e., activity, against *Clostridium* including *Clostridium difficile*. Therefore, compounds of the invention can be used to treat infections associated with *C. difficile*, e.g., pseudomembraneous colitis, toxic megacolin, and other antibiotic associated diarrheas (AAD).

Compounds of the present invention are not, however, active against mammalian cells. This provides an optimal combination of high activity against pathogenic bacteria and low or no activity against mammalian cells, allowing for the use of these compounds in mammalian treatments.

Bacterial infections which may be treated include gastrointestinal tract infections, respiratory tract infections, otitis media, meningitis, endocarditis, skin and soft tissue infections in man, mastitis in cattle, and also respiratory infections in farm animals such as pigs and cattle.

Accordingly, in a further aspect, the present invention provides a method of treating bacterial infection in human or non-human animals, which method comprises administering a therapeutically effective amount of a compound of formula (I)-(XI) as hereinbefore defined, to a human or non-human animal in need of such therapy. Compounds of the invention can be combined with other known antibacterial agents or can be combined together, e.g., a treatment having a combination of compounds of formula (VIII) and (IX). It will be appreciated that a compound of the present invention which has a broad spectrum of antibacterial activity, including activity against both Gram positive and Gram negative bacteria will be of general use in the community for the empiric treatment of community acquired infections. In comparison, a compound of the present invention with a more limited spectrum, for instance activity against Gram positive bacteria, is more likely to be used in circumstances where the causative pathogenic organism has been identified.

The present invention provides a pharmaceutical composition comprising a compound of formula (I)-(XI) together with a pharmaceutically acceptable carrier or excipient.

The present invention further provides pharmaceutical compositions comprising combinations of compounds of formula (I)-(XI) together with a pharmaceutically acceptable carrier or excipient. For example, a pharmaceutical composition of the invention can include a compound of formula (VII) and a compound of formula (IX) in combination with the carrier or excipient.

The present invention also provides a method of treating bacterial infections in mammals, especially in humans and in domesticated animals, which comprises administering a compound of formula (I)-(XI), or a composition according to the invention, to a patient in need thereof. In some embodiments the bacterial infection is a *Clostridium* based infection and often is a *Clostridium difficile* infection.

The invention further provides the use of a compound of formula (I)-(XI) in the preparation of a medicament composition for use in the treatment of bacterial infections.

The compounds and compositions according to the invention may be formulated for administration in any convenient way for use in human or veterinary medicine, by analogy with other antibiotics.

The compounds and compositions according to the invention may be formulated for administration by any route, for example oral, topical, parenteral, or rectal. The compositions may, for example, be made up in the form of tablets, capsules, powders, granules, lozenges, creams, suppositories, ointments, gels, lotions, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrollidone; fillers, for example lactose, sucrose, maize-starch, calcium phosphate, sorbitol or glycine; tabletting lubricants, for example magnesium stearate, talc, polyethylene glycol or silica; disintegrants, for example potato starch; pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, impregnated dressings, and aerosols, and may contain appropriate conventional additives, including, for example, preservatives, solvents to assist drug penetration, and emollients in ointments, gels, and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilized before being filled into a suitable vial or ampoule, which is then sealed. Advantageously, conventional additives including, for example, local anesthetics, preservatives, and buffering agents can be dissolved in the vehicle. In order to enhance the stability of the solution, the composition may be frozen after being filled into the vial, and the water removed under vacuum; the resulting dry lyophilized powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterilization cannot be accomplished by filtration. The compound may instead be sterilized by exposure to ethylene oxide before being suspended in the sterile vehicle. Advantageously, a surfactant or wetting agent is included in such suspensions in order to facilitate uniform distribution of the compound.

A compound or composition according to the invention may suitably be administered to the patient in an antibacterially effective amount. In some cases the compounds and compositions according to the invention are administered in an amount effective to treat a patient with a *Clostridium* infection and in particular a *Clostridium difficile* infection.

A composition according to the invention may suitably contain from 0.1% by weight, preferably from 10 to 60% by weight, of a compound according to the invention (based on the total weight of the composition), depending on the method of administration.

The compounds according to the invention may suitably be administered to the patient at a daily dosage of from 1.0 to 100 mg/kg of body weight. For an adult human (of approximately 70 kg body weight), from 50 to 3000 mg, for example about 1500 mg, of a compound according to the invention may be administered daily. Suitably, the dosage for adult humans is from 5 to 40 mg/kg per day. Higher or lower dosages may, however, be used in accordance with normal clinical practice.

When the compositions according to the invention are presented in unit dosage form, each unit dose may suitably comprise from 25 to 1000 mg, preferable from 50 to 500 mg, of a compound according to the invention.

EXAMPLES

The following examples are provided for illustrative purposes only and are not intended to limit the scope of the invention.

Example 1

Synthetic Methods

Chiral Separation and Catalytic Asymmetric Synthesis

The following examples and experiments describe the manner and process of making and using the present invention and are illustrative rather than limiting. The compounds of the present invention, salts thereof, and their intermediates can be prepared or manufactured as described herein or by various processes known to be present in the chemical art.

Process 1: Synthesis Via Chiral Separation:

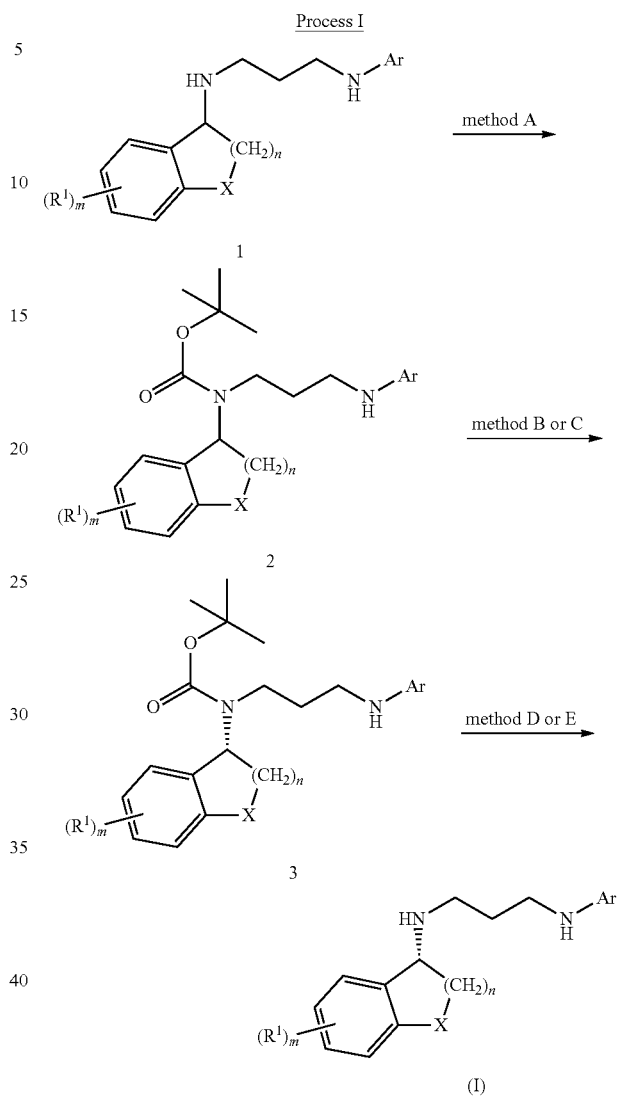

Method A:

Preparation of (6,8-Dibromo-chroman-4-yl)-[3-(7-oxo-4,7-dihydro-thieno[3,2-b]pyridin-5-ylamino)-propyl]-carbamic acid tert-butyl ester

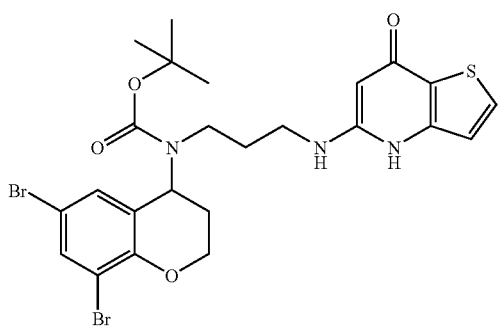

The 5-[3-(6,8-Dibromo-chroman-4-ylamino)-propylamino]-4H-thieno[3,2-b]pyridin-7-one was prepared as a racemic mixture according to methods described in U.S. patent application Ser. No. 11/853,314, entitled "Substituted Thienopyridone Compounds with Antibacterial Activity," filed Sep. 11, 2007 and combined with tetrahydrofuran (0.02M) and 1.5 equivalent of sodium hydride (as a 60% suspension in mineral oil). The reaction was allowed to stir 30 minutes at room temperature and 1.04 equivalents of Boc-anhydride was added portion-wise. After addition was complete, the reaction was allowed to stir overnight. Solvent was removed and the crude material was purified by silica gel column chromatography, eluting with 0-100% gradient of ethyl acetate and hexanes to give the title compound as a yellow oil.

Method B:

Racemic mixtures described above were separated into the single enantiomers by preparative chiral chromatography (prep-HPLC). For (6,8-Dibromo-chroman-4-yl)-[3-(7-oxo-4,7-dihydro-thieno[3,2-b]pyridin-5-ylamino)-propyl]-carbamic acid tert-butyl ester, 300 mg batches of the first (R-(+)-enantiomer (formula IX)) and second (S-(−)-enantiomer) eluting enantiomer were isolated, both with e.e. >99%.

| PREPARATIVE HPLC CONDITIONS | |
|---|---|
| Column: | Chiralpak AD; 250 × 20 mm; Diacel Chemical Industries LTD |
| Eluent: | Heptane/EtOH (90/10) |
| Flow: | 6.0 ml/min |
| UV: | 256 nm |
| Sample: | 50 mg/ml |
| Injection volume: | 500 μl |
| Retention Time: | R-(+)-enantiomer, ~37 min. |
|  | S-(−)-enantiomer, ~47 min. |

| ANALYTICAL HPLC CONDITIONS | |
|---|---|
| Column: | Chiralcel OD-H; 150 × 4.6 mm; Diacel Chemical Industries LTD |
| Eluent: | Heptane/IPA (90/10) |
| Flow: | 0.5 ml/min |
| UV: | 256, 328 nm |
| Sample: | ~1 mg/ml |
| Injection volume: | 20 μl |
| Retention Time: | R-(+)-enantiomer, ~41 min. |
|  | S-(−)-enantiomer, ~46 min. |

Method C:

Racemic mixtures of tert-butyl 6,8-dibromo-1,2,3,4-tetrahydroquinolin-4-yl(3-(7-oxo-4,7-dihydrothieno[3,2-b]pyridin-5-ylamino)propyl)carbamate prepared similarly as in method A were separated into single enantiomers by preparative chiral chromatography (prep-HPLC). A 113 mg batch of the first eluting enantiomer (formula VIII, R-(+)-enantiomer, e.e. >99%) and a 70 mg batch of the second eluting enantiomer (S-(−)-enantiomer, e.e. 85%) were isolated. Further purification of this second eluting enantiomer by a second preparative run afforded 5.5 mg of this enantiomer with e.e. >99%.

| PREPARATIVE HPLC CONDITIONS | |
|---|---|
| Column: | Chiralcel OD-H; 250 × 20 mm; Diacel Chemical Industries LTD |
| Eluent: | Heptane/EtOH/Et₂NH (95/5/0.2%) |
| Flow: | 10 ml/min |
| UV: | 256, 328 nm |
| Sample: | 85 mg/ml |
| Injection volume: | 80 μl |

| ANALYTICAL HPLC CONDITIONS | |
|---|---|
| Column: | Chiralcel OD-H; 150 × 4.6 mm; Diacel Chemical Industries LTD |
| Eluent: | Heptane/IPA (90/10) |
| Flow: | 0.5 ml/min |
| UV: | 256, 328 nm |
| Sample: | ~1 mg/ml |
| Injection volume: | 20 μl |
| Retention Time: | R-(+)-enantiomer, ~41 min. |
|  | S-(−)-enantiomer, ~46 min. |

Method D:

The ((R)(+)-6,8-Dibromo-chroman-4-yl)-[3-(7-oxo-4,7-dihydro-thieno[3,2-b]pyridin-5-ylamino)-propyl]-carbamic acid tert-butyl ester was taken up in 4.0M HCl in dioxane and allowed to stir overnight, during which the product oiled out of solution. About half of the dioxane was removed via evaporation and the remaining was stirred for several hours. Product precipitated out of solution as an off-white solid (this solid was isolated by vacuum filtration and dried under vacuum to give the title compound as an off-white solid).

Method E:

The ((R)(+)-6,8-Dibromo-1,2,3,4-tetrahydro-quinolin-4-yl)-[3-(7-oxo-4,7-dihydro-thieno[3,2-b]pyridin-5-ylamino)-propyl]-carbamic acid tert-butyl ester was treated with HCl (4.0M solution prepared with concentrated HCl in THF). This was allowed to stir overnight. The solvent was removed via evaporation and the resulting white solid was stirred with ether. The solid was isolated by vacuum filtration. Solid was isolated and dried under vacuum to give title compound as a white solid (this solid was isolated by vacuum filtration and dried under vacuum to give the title compound as an off-white solid).

Process II: Synthesis Via Asymmetric Reduction

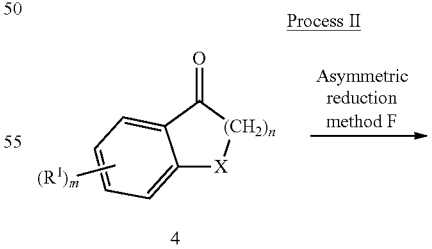

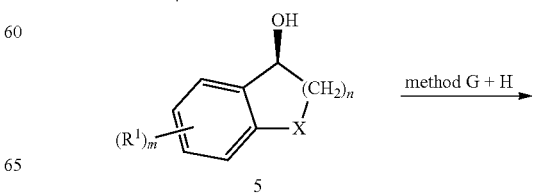

-continued

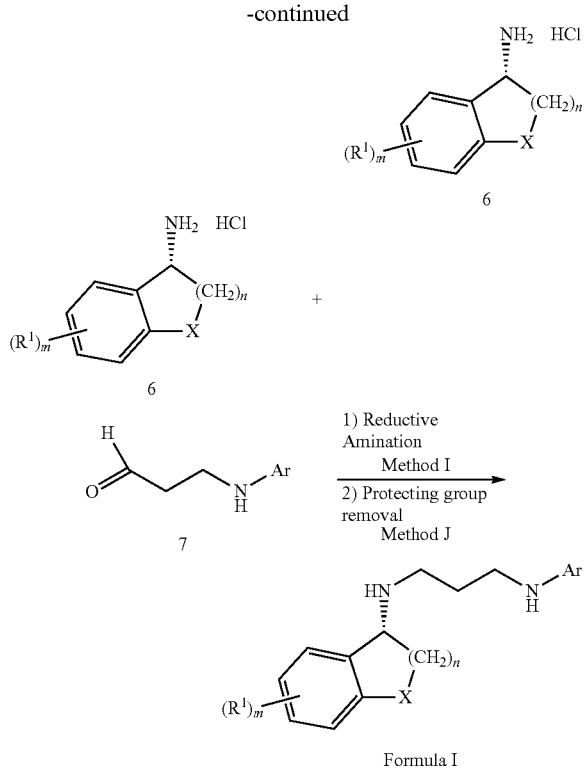

Formula I

Preparation of 5-(3-oxopropylamino)thieno[3,2-b]pyridin-7-yl benzoate HCl salt, an example of compound 7

Preparation of intermediate 2,2-Dimethyl-5-(methylsulfanyl-thiophene-3-ylamino-methylene)-[1,3]dioxane-4,6-dione 3-Thiophene isothiocyanate (472.5 g, 3.34 mol) was mixed with 2,2-dimethyl-1,3-dioxane-4,6-dione (433.2 g, 3.006 mol) in dimethylsulfoxide (1.9 L). Triethylamine (516 mL, 3.67 mol) was added dropwise over 130 min. while maintaining the reaction temperature below 20° C. After the addition, the resultant mixture was stirred at room temperature for 16 h. Iodomethane (426.7 g, 3.006 mol) was added slowly over 70 min while the reaction temperature was maintained below 20° C. After complete addition, the mixture was stirred at room temperature for 1 h. A dilute aqueous hydrochloric acid solution (4.8 L of water containing 46 mL of 37% HCl) was slowly added to precipitate the product while the temperature was kept below 30° C. The mixture was stirred for 2 h. The solids were filtered and rinsed with water. The resultant wet solids were suspended in EtOH (6 L) and then the solvents were removed under reduced pressure. The resultant slurry was dissolved in boiling methanol (4.0 L) and treated with decolorizing charcoal (Norit brand, 130 g) and maintained at reflux for 40 min. The hot solution was filtered through a pad of Celite 543 and the filter cake rinsed with boiling methanol (1 L). The filtrate was allowed to stand at room temperature for 24 h. The solids were filtered and dried to afford 408.4 g (45%) of light brown crystals of the intermediate 2,2-Dimethyl-5-(methylsulfanyl-thiophene-3-ylamino-methylene)-[1,3]dioxane-4,6-dione. $^1$H NMR (400 MHz, CDCl$_3$) δ 1.76 (s, 6H), 2.38 (s, 3H), 7.09 (d, 1H J=5 Hz), 7.25 (d, 1H, J=3.2 Hz), 7.38 (dd, 1H, J=3.2, 5 Hz), 12.7 (br s, 1H).

Preparation of intermediate 5-((3,3-Diethoxypropylamino)(thiophene-3-ylamino)methylene)-2,2-dimethyl-1,3-dioxane-4,6-dione 3,3-Diethoxypropylamine (210.7 g, 1.43 mol) was added in portions to the solution of 2,2-dimethyl-5-(methylsulfanyl-thiophene-3-ylamino-methylene)-[1,3]dioxane-4,6-dione (407.3 g, 1.36 mol) in dichloromethane (1.7 L) and methanol (0.36 L) over 60 min, while the reaction temperature was kept under 25° C. with a water bath. After stirring for 1.5 h at room temperature, the reaction mixture was diluted with dichloromethane (0.8 L). The organic layer was separated and washed with aqueous ammonium chloride solution (400 mL, made of 200 mL of sat. NH$_4$Cl and 200 mL of water), brine (300 mL) and dried over magnesium sulfate. Concentration of the reaction mixture under reduced pressure afforded a dark oil. Xylenes (500 ml) were added and the mixture concentrated under reduced pressure to give the intermediate 5-((3,3-Diethoxypropylamino)(thiophene-3-ylamino)methylene)-2,2-dimethyl-1,3-dioxane-4,6-dione. The resultant dark oil was used directly in next step without further purification. $^1$H NMR (400 MHz, CDCl$_3$) δ 1.65 (m, 6H), 1.73 (s, 6H), 1.78 (m, 2H), 2.98 (q, 2H, J=6.4 Hz), 3.45 (m, 2H), 3.60 (m, 2H), 4.50 (t, 1H, J=5.2 Hz), 6.98 (dd, 1H, J=1.6, 5.2 Hz), 7.05 (dd, 1H, J=1.2, 3.2 Hz), 7.33 (dd, 1H, J=3.2, 5.2 Hz), 10.2 (s, 1H), 11.3 (s, 1H).

Preparation of intermediate 5-(3,3-Diethoxypropylamino)-7-oxo-4,7-dihydrothieno[3,2-b]pyridine-6-carboxylic acid 5-((3,3-Diethoxypropylamino)(thiophene-3-ylamino)methylene)-2,2-dimethyl-1,3-dioxane-4,6-dione (1.62 mol) was suspended in a solution of hexamethyldisilazane (1.08 L, 5.18 mol) in xylenes (2.4 L) and was heated at reflux for 24 h. After cooling to room temperature, the mixture was concentrated under reduced pressure to afford a dark oil. The dark oil was carefully treated with methanol (0.5 L) to form brown solids, followed by addition of ethyl ether (1.6 L). The resultant solids were filtered and washed with MeOH/Ether (1:3) (0.8 L). The solids were dried under vacuum to afford 432.2 g (78%) of the desired intermediate 5-(3,3-Diethoxypropylamino)-7-oxo-4,7-dihydrothieno[3,2-b]pyridine-6-carboxylic acid as a beige solid. $^1$H NMR (400 MHz, DMSO d$_6$) δ 1.09 (m, 6H), 1.91 (m, 2H), 3.40 (m, 2H), 3.58 (m, 2H), 4.06 (s, 1H), 4.60 (t, 1H, J=5.2 Hz), 7.28 (d, 1H, J=4.8 Hz), 8.05 (d, 1H, J=4.8 Hz), 9.94 (m, 1H), 11.8 (s, 1H).

Preparation of the intermediate Sodium 5-(3,3-diethoxypropylamino)thieno[3,2-b]pyridin-7-olate 5-(3,3-Diethoxypropylamino)-7-oxo-4,7-dihydrothieno[3,2-b]pyridine-6-carboxylic acid (432 g, 1.27 mol) was mixed with sodium methoxide (95% pure, 75.8 g, 1.33 mol) and suspended in xylenes (2 L). The resultant mixture was heated at reflux for 2 h. The reaction mixture was gradually cooled to room temperature with stirring to afford light brown solids. The solids were collected by filtration and washed with toluene and dried under vacuum at 50-60° C. for 48 h to give the desired intermediate sodium 5-(3,3-diethoxypropylamino)thieno[3,2-b]pyridin-7-olate (a solid). This crude product was used in the next step without further purification. $^1$H NMR (400 MHz, DMSO d$_6$) δ 1.08 (m, 6H), 1.72 (q, 2H, J=6.8 Hz), 3.15 (m, 2H), 4.55 (t, 1H, J=6 Hz), 6.22 (s, 1H), 6.98 (d, 1H, J=5.2 Hz), 7.53 (d, 1H, J=5.2 Hz).

Preparation of the intermediate 5-(3,3-Diethoxypropylamino)thieno[3,2-b]pyridin-7-yl benzoate Sodium 5-(3,3-diethoxypropylamino)thieno[3,2-b]pyridin-7-olate (445.7 g, 1.40 mol) was suspended in DMSO (2.8 L). Benzoic anhydride (332.9 g, 1.47 mol) was added in portions at room temperature. After the addition, the reaction mixture was stirred for 3 h at room temperature. The mixture was diluted with ethyl acetate (6 L). The resultant organic solution was washed with water (6 L). The separated aqueous layer was extracted with ethyl acetate (2 L). The combined organic layers were dried over magnesium sulfate and filtered. Removal of solvent under reduced pressure and drying under vacuum afforded the desired intermediate 5-(3,3-Diethoxypropylamino)thieno[3,2-b]pyridin-7-yl benzoate as a dark oil. This product was used in the next step without further purification. $^1$H NMR (400 MHz, CDCl$_3$) δ 1.09 (m, 6H), 1.99 (m, 2H), 3.50 (m, 4H), 3.70 (m, 2H), 4.60 (t, 1H, J=5.6 Hz), 7.30 (d, 1H, J=4.8 Hz), 7.55 (m, 3H), 7.67 (d, 1H, J=4.8 Hz), 8.24 (m, 2H).

Preparation of the title compound 5-(3-oxopropylamino)thieno[3,2-b]pyridin-7-yl benzoate HCl salt, an example of compound 7

The crude 5-(3,3-diethoxypropylamino)thieno[3,2-b]pyridin-7-yl benzoate from above (677.3 g, 1.68 mol) was dissolved in 3.0 L of THF. Then, 12N HCl (1.68 mol, 0.14 L) was added dropwise while the reaction temperature was maintained below 20° C. with an ice-water bath. After stirring for 5 minutes, solids precipitated. The resultant mixture was stirred at room temperature for 1 h, followed by the addition of ethyl acetate (2.0 L). The mixture was stirred for 30 min. The solids were filtered, rinsed with ethyl acetate (250 ml×2), and then dried under reduced pressure at 55° C. to give the title compound 5-(3-oxopropylamino)thieno[3,2-b]pyridin-7-yl benzoate HCl salt as a light brown solid. $^1$H NMR (400 MHz, DMSO d$_6$) δ 2.20 (m, 2H), 3.56 (m, 2H), 6.31 (t, 1H, J=3.6 NHz), 7.83-7.87 (m, 2H), 7.96 (d, 1H, J=6.0 Hz), 8.16-8.20 (m, 2H), 8.35 (d, 1H, J=5.6 Hz), 10.20 (s, 1H).

Method F:

Preparation of 6,8-Dibromo-chroman-4(S)-ol

To a mixture containing 6,8-dibromochroman-4-one in acetonitrile (0.3M) and 5/2 formic acid/triethylamine (30% by volume) was added (1S,2S)-(+)-N-p-tosyl-1,2-diphenylethylene diamine (1 mol %) and dichloro(p-cymene)-ruthenium (II) dimer (0.5 mol %). After stirring for 24 h, the reaction was diluted with ethylacetate and washed with brine/sodium bicarbonate (1:1). The organic phase was concentrated under reduced pressure to afford the title compound as a tan solid.

$^1$H NMR (400 MHz, CDCl$_3$) δ 7.59 (d, 1H), 7.41 (d, 1H), 4.78 (ABq, 1H), 4.38 (m, 2H), 2.08 (m, 2H), 1.91 (d, 1H).

Method G:

Preparation of 4(R)-Azido-6,8-dibromo-chroman

A solution containing 6,8-dibromo-chroman-4(S)-ol in tetrahydrofuran (0.17M) and 1.2 equivalents of diphenylphosphorylazide was stirred for 15 minutes at room temperature. The solution was cooled to 10° C. and 2.5 equivalents of 1,8-diazabicyclo[5.4.0]undec-7-ene added. The mixture was stirred with gradual warming to room temperature and maintained for 48 h. The mixture was diluted with ethylacetate and washed with brine followed by water. The organic phase was concentrated to afford the title compound as a tan oil.

$^1$H NMR (400 MHz, CDCl$_3$) δ 7.65 (d, 1H), 7.32 (d, 1H), 4.57 (t, 1H), 4.43 (m, 1H), 4.31 (m, 1H), 2.18 (m, 1H), 2.08 (m, 1H).

Method H:

Preparation of 6,8-Dibromo-chroman-4(R)-ylamine hydrochloride

To an ice cooled solution of 4(R)-azido-6,8-dibromo-chroman in tetrahydrofuran (0.16M) was added 1.2 equivalents of trimethylphosphine. The mixture was warmed to room temperature and maintained for 16 h. Concentration of the mixture gave the crude amine. This was dissolved in acetonitrile (0.20M) and 2 equivalents of hydrochloric acid added. The mixture was stirred for 16 h and the solids filtered, washed with acetonitrile and dried to afford the title compound as an off-white solid.

$^1$H NMR (400 MHz, CD$_3$OD) δ 7.75 (d, 1H), 7.60 (dd, 1H), 4.62 (t, 1H), 4.40 (m, 2H), 2.40 (m, 1H), 2.20 (m, 1H).

Method I:

Preparation of 5-[3-(6,8-Dibromo-chroman-4-ylamine) propylamino]-thieno[3,2-b]pyridin-7-yl benzoate 5-(3-Oxopropylamine)thieno[3,2-b]pyridine-7-yl benzoate hydrochloride salt was mixed with 1 equivalent of 6,8-dibromo-chroman-4(R)-ylamine hydrochloride in tetrahydrofuran (0.35M) followed by the addition of 3 equivalents of triethylamine. After stirring for 1 h, 1.3 equivalents of sodium triacetoxyborohydride was added and the mixture stirred for 2 h. The reaction was diluted with ethylacetate and washed with aqueous sodium bicarbonate. The organic phase was dried over magnesium sulfate. Filtration, removal of solvent and purification of the crude product by column chromatography eluting with 0-10% methanol in dichloromethane gave the title compound as a brown oil.

$^1$H NMR (400 MHz, CDCl$_3$) δ 8.24 (m, 2H), 7.70 (m, 1H), 7.56 (m, 3H), 7.50 (d, 1H), 7.40 (d, 1H), 7.24 (d, 1H), 6.58 (m, 1H), 4.34 (m, 2H), 3.77 (t, 1H), 3.56 (m, 2H), 2.85 (m, 2H), 2.0 (m, 2H)

Method J:

Preparation of 5-[3-(6,8-Dibromo-chroman-4-ylamine) propylamino]-4H-thieno[3,2-b]pyridin-7-one di-hydrochloride To a solution containing 5-[3-(6,8-dibromo-chroman-4-ylamine) propylamino]-thieno[3,2-b]pyridin-7-yl benzoate in ethylacetate (2.5M) and tetrahydrofuran (1.2M) was added 2.5 equivalents of 2M ammonia in methanol. After stirring for 24 h, the mixture was diluted with ethylacetate and solids filtered, rinsed with ethylacetate and dried. Purification of the crude material by column chromatography eluting with 0-10% ammonia/methanol in dichloromethane gave the title compound as the free base. This was dissolved in absolute ethanol (0.4M) and 3 equivalents of 4N hydrochloric acid added. The mixture was heated to 75° C. and treated with decolorizing charcoal. The resultant mixture was filtered through a pad of Celite and the filter bed was rinsed with warm ethanol/4N hydrochloric acid. The filtrate was stirred over 16 h at room temperature until colorless solids formed. The solids were filtered, rinsed with ethanol/2N hydrochloric acid and dried under vacuum at 95-100° C. to yield the target compound as an off-white solid.

$^1$H NMR (400 MHz, CD$_3$OD): δ8.04 (d, 1H), 7.77 (s, 1H), 7.71 (s, 1H), 7.45 (d, 1H), 6.26 (s, 1H), 4.62 (br, s, 1H), 4.52-4.38 (m, 2H), 3.59 (t, 2H), 3.41 (m, 1H), 3.28 (m, 1H), 2.41 (m, 2H), 2.18 (m, 2H).

Example 2

Synthesis of 5-[3-((R)(+)6,8-Dibromo-chroman-4-ylamino)-propylamino]-4H-thieno[3,2-b]pyridin-7-one di-hydrochloride (formula IX, a compound of the invention)

Using the synthesis reactions as described in Process I (methods A, B and D), the title compound was prepared and isolated as the first eluting enantiomer. Alternatively the title compound was prepared according to Process II (methods F-J). The title compound was isolated as an off-white solid in both instances.

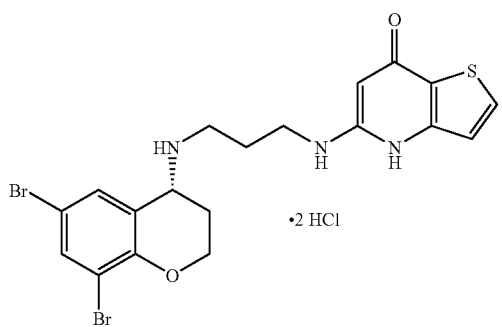

$^1$H NMR (400 MHz, CD$_3$OD): δ8.04 (d, 1H), 7.77 (s, 1H), 7.71 (s, 1H), 7.45 (d, 1H), 6.26 (s, 1H), 4.62 (br, s, 1H), 4.52-4.38 (m, 2H), 3.59 (t, 2H), 3.41 (m, 1H), 3.28 (m, 1H), 2.41 (m, 2H), 2.18 (m, 2H). MS (ES+): M/Z 514 (M+1). Optical rotation: $[\alpha]_{589}$=+23.06 (c=0.503 mM in MeOH, 20° C.).

Co-crystals of 5-[3-((R)(+)6,8-Dibromo-chroman-4-ylamino)-propylamino]-4H-thieno[3,2-b]pyridin-7-one di-hydrochloride (formula IX) and *Clostridium difficile* MetRS were grown. X-ray diffraction of the co-crystals provided a 1.72 Å resolution pattern. The three dimensional structure of compound IX was unambiguously assigned R absolute configuration.

Example 3

Synthesis of 5-[3-((S)(−)-6,8-Dibromo-chroman-4-ylamino)-propylamino]-4H-thieno[3,2-b]pyridin-7-one di-hydrochloride (comparative compound)

Using the synthesis reactions as described in Process 1 (methods A, B and D), the title compound was prepared and isolated as the second eluting enantiomer. Alternatively the title compound was prepared according to Process II wherein in Method F, the (1R,2R)-(−)-N-p-tosyl-1,2-diphenylethylene diamine (1 mol %) and dichloro(p-cymene)-ruthenium (II) dimer was employed, followed by methods G-J. The title compound was isolated as an off-white solid in both instances.

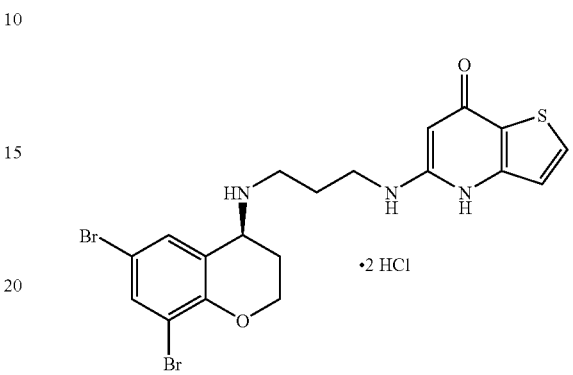

$^1$H NMR (400 MHz, CD$_3$OD): δ8.04 (d, 1H), 7.77 (s, 1H), 7.71 (s, 1H), 7.45 (d, 1H), 6.26 (s, 1H), 4.62 (br, t, 4.52-4.38 (m 2H), 3.59 (t, 2H), 3.41 (m, 1H), 3.27 (m, 1H), 2.41 (m, 2H), 2.17 (m, 2H). MS (ES+): M/Z 514 (M+1). Optical rotation: $[\alpha]_{589}$=−21.70 (c=0.507 mM in MeOH, 20° C.).

Example 4

Synthesis of 5-[3-((R)(+)-8-Bromo-6-chloro-chroman-4-ylamino)-propylamino]-4H-thieno[3,2-b]pyridin-7-one di-hydrochloride (formula VII, a compound of the invention)

Using the synthesis reactions as described in Example 1 (methods A, B and D), the title compound was prepared and isolated as the first eluting enantiomer:

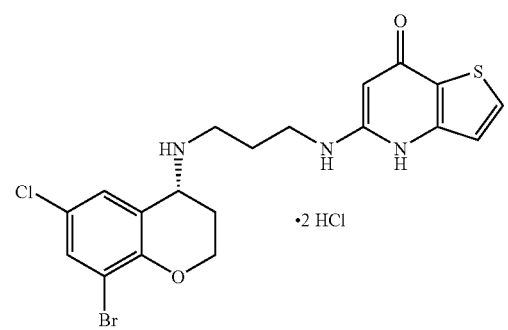

$^1$H NMR (400 MHz, CD$_3$OD): δ8.05 (d, 1H), 7.66 (s, 1H), 7.56 (s, 1H), 7.43 (d, 1H), 6.25 (s, 1H), 4.62 (t, 1H), 4.52-4.38 (m, 2H), 3.58 (t, 2H), 3.39 (m, 1H), 3.29 (m, 1H), 2.41 (m, 2H), 2.17 (m, 2H). MS (ES+): M/Z 470 (M+1). Optical rotation: $[\alpha]_{589}$=+36.86 (c=0.510 mM in MeOH, 20° C.).

Example 5

Synthesis of 5-[3-((S)(−)-8-Bromo-6-chloro-chroman-4-ylamino)-propylamino]-4H-thieno[3,2-b]pyridin-7-one di-hydrochloride (comparative compound)

Using the synthesis reactions as described in Process 1 (methods A, B and D), the title compound was prepared and isolated as the second eluting enantiomer:

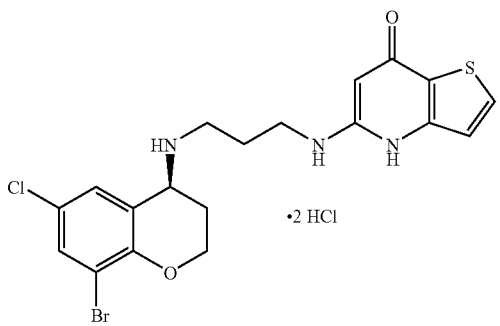

$^1$H NMR (400 MHz, CD$_3$OD): δ 8.05 (d, 1H), 7.66 (s, 1H), 7.59 (s, 1H), 7.45 (d, 1H), 6.26 (s, 1H), 4.63 (t, 1H), 4.52-4.38 (m, 2H), 3.57 (t, 2H), 3.41 (m, 1H), 3.30 (m, 1H), 2.42 (m 2H), 2.18 (m 2H). MS (ES+): M/Z 470 (M+1). Optical rotation: $[\alpha]_{589}$=−35.24 (c=0.500 mM in MeOH, 20° C.).

Example 6

Synthesis of 2-[3-((R)(+)-6,8-Dibromo-chroman-4-ylamino)-propylamino]-1H-quinolin-4-one di-hydrochloride (formula X, a compound of the invention)

Using the synthesis reactions as described in Example 1 (methods A, B and D), the following compound was prepared and isolated as the first eluting enantiomer:

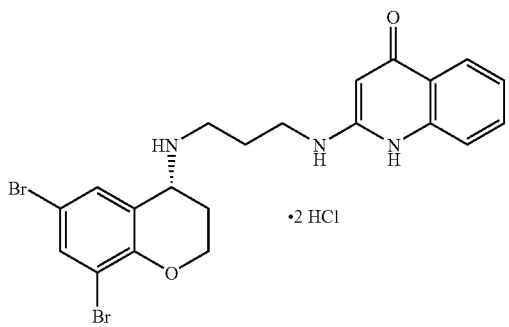

$^1$H NMR (400 MHz, CD$_3$OD): δ 8.10 (d, 1H), 7.90 (br, 1H), 7.78-7.75 (m, 3H), 7.48 (t, 1H), 6.38 (s, 1H), 4.65 (t, 1H), 4.48 (m, 2H), 3.70 (m, 2H), 3.44 (m, 1H), 3.31 (m, 1H), 2.48 (m, 1H), 2.40 (m, 1H), 2.23 (m, 2H). MS (ES+): M/Z 508 (M+1). Optical rotation: $[\alpha]_{589}$=+23.22 (c=0.500 mM in MeOH, 20° C.).

Example 7

Synthesis of 2-[3-((S)(−)-6,8-Dibromo-chroman-4-ylamino)-propylamino]-1H-quinolin-4-one di-hydrochloride (comparative compound)

Using the synthesis reactions as described in Example 1 (methods A, B and D), the following compound was prepared and isolated as the second eluting enantiomer:

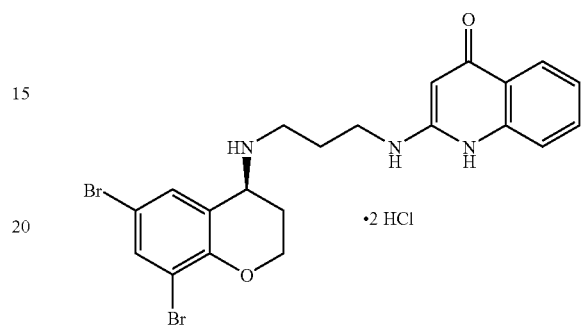

$^1$H NMR (400 MHz, CD$_3$OD): δ 8.10 (d, 1H), 7.90 (br, 1H), 7.78-7.75 (m, 3H), 7.48 (t, 1H), 6.38 (s, 1H), 4.65 (t, 1H), 4.48 (m, 2H), 3.70 (m, 2H), 3.44 (m, 1H), 3.31 (m, 1H), 2.48 (m, 1H), 2.40 (m, 1H), 2.23 (m, 2H). MS (ES+): M/Z 508 (M+1). Optical rotation: $[\alpha]_{589}$=−24.51 (c=0.506 mM in MeOH, 20° C.).

Example 8

Synthesis of 5-[3-((R)(+)-6,8-Dibromo-1,2,3,4-tetrahydro-quinolin-4-ylamino)-propylamino]-4H-thieno[3,2-b]pyridin-7-one tri-hydrochloride (formula VIII, a compound of the invention)

Using the synthesis reactions as described in Examples 1 (Methods A, C and E), the following compound was prepared and isolated as the first eluting enantiomer. Alternatively the title compound was prepared according to Process II (methods F-J). The title compound was isolated as an off-white solid in both instances.

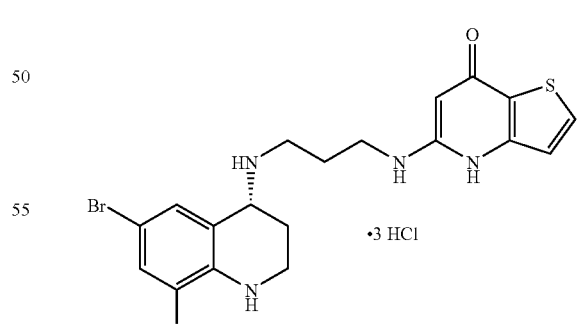

$^1$H NMR (400 MHz, CD$_3$OD): δ 8.05 (d, 1H), 7.58 (s, 1H), 7.44 (d, 1H), 7.42 (s, 1H), 6.25 (s, 1H), 4.48 (br, s, 1H), 3.63-3.53 (m, 4H), 3.38 (m, 1H), 3.21 (m, 1H), 2.43 (m, 1H), 2.14 (m, 2H), 2.07 (m, 1H). MS (ES+): M/Z 513 (M+1). Optical rotation: $[\alpha]_{589}$=+72.26 (c=0.507 mM in MeOH, 20° C.).

Example 9

Synthesis of 5-[3-((S)(−)-6,8-Dibromo-1,2,3,4-tetrahydro-quinolin-4-ylamino)-propylamino]-4H-thieno[3,2-b]pyridin-7-one tri-hydrochloride (comparative compound)

Using the synthesis reactions as described in Examples 1 (Methods A, C and E), the following compound was prepared and isolated as the second eluting enantiomer. Alternatively the title compound was prepared according to Process II wherein in Method F, the (1R,2R)-(−)-N-p-tosyl-1,2-diphenylethylene diamine (1 mol %) and dichloro(p-cymene)-ruthenium (II) dimer was employed, followed by methods G-J. The title compound was isolated as an off-white solid in both instances.

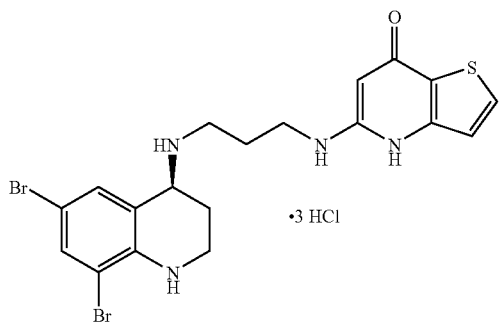

$^1$H NMR (400 MHz, CD$_3$OD): δ 8.04 (d, 1H), 7.58 s, 1H), 7.43 (d, 1H), 7.42 (s, 1H), 6.23 (s, 1H), 4.48 (br, s, 1H), 3.63-3.52 (m, 4H), 3.37 (m, 1H), 3.22 (m, 1H), 2.42 (m, 1H), 2.20-2.00 (m, 3H). MS (ES+): M/Z 513 (M+1).

Example 10

5-[3-((R)-5,7-Dibromo-1,2,3,4-tetrahydro-naphthalen-1-ylamino)-propylamino]-4H-thieno[3,2-b]pyridine-7-one (formula VI, a compound of the invention)

The title compound was prepared according to Process II (methods F-J). The title compound was isolated as an off-white solid.

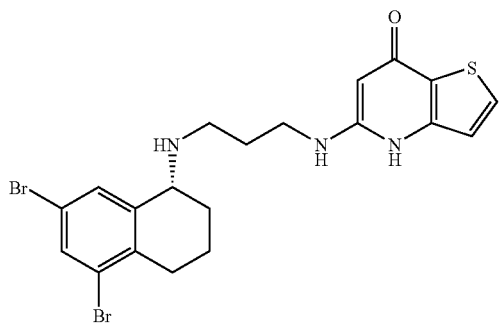

$^1$H NMR (400 MHz, CD$_3$OD): δ 7.68 (d, 1H), 7.59 (d, 2H), 7.00 (d, 1H), 5.57 (s, 1H), 3.80 (t, 1H), 3.32 (t, 2H), 2.76 (m, 3H), 2.61 (m, 1H), 1.97 (m, 1H), 1.86 (m, 4H), 1.72 (m, 1H). MS (ES+): M/Z 512 (M+1). Optical rotation: [α]$_{589}$=−22.30 (c=0.870 mM in MeOH, 20° C.).

Example 11

5-[3-((S)-5,7-Dibromo-2,3-dihydro-benzofuran-3-ylamino)-propylamino]-4H-thieno[3,2-b]pyridine-7-one (formula XI, a compound of the invention)

The title compound was prepared according to Process II (methods F-J). The title compound was isolated as an off-white solid.

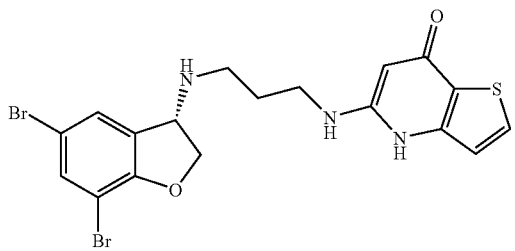

$^1$H NMR (400 MHz, CD$_3$OD): δ 7.69 (d, 1H), 7.46 (d, 2H), 7.06 (d, 1H), 5.54 (s, 1H), 4.60 (m, 2H), 4.47 (m, 1H), 3.30 (m, 2H), 2.73 (m, 1H), 2.61 (m, 1H), 1.80 (m, 2H). MS (ES+): M/Z 500 (M+1). Optical rotation: [α]$_{589}$=−1.93 (c=0.725 mM in MeOH, 20° C.).

Example 12

5-[3-((R)-5,7-Dibromo-2,3-dihydro-benzofuran-3-ylamino)-propylamino]-4H-thieno[3,2-b]pyridine-7-one (comparative compound)

The title compound was prepared according to Process II wherein in Method F, the (1R,2R)-(−)-N-p-tosyl-1,2-diphenylethylene diamine (1 mol %) and dichloro(p-cymene)-ruthenium (II) dimer was employed, followed by methods G-J. The title compound was isolated as an off-white solid.

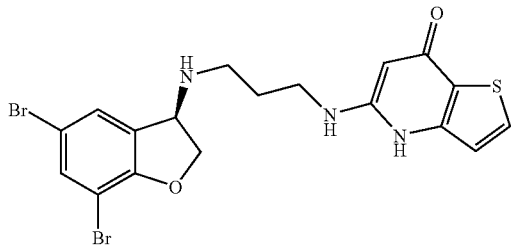

$^1$H NMR (400 MHz, CD$_3$OD): δ 7.70 (d, 1H), 7.48 (d, 2H), 7.06 (d, 1H), 5.56 (s, 1H), 4.63 (m, 2H), 4.50 (dd, 1H), 3.30 (m, 2H), 2.75 (m, 1H), 2.63 (m, 1H), 1.81 (m, 2H). MS (ES+): M/Z 500 (M+1).

Example 13

Expression and Purification of MetRS

The following example illustrates expression and purification of *C. difficile* MetRS useful in the functional assays shown in examples 14 and 15.

Cloning of Over-producing Vector: N-terminally hexaHis-tagged *C. difficile* MetRS was amplified and cloned into pET-coco-2. The following primers were used to amplify DNA from genomic DNA: 5'-CTGCAGAGCTAGCAAAC-CGAGTTTTTATGTAAC-3' (forward) (SEQ ID NO:1), 5'-CTTTCTAAGCTTCTACTAACGAACCTCGGATCC-3' (reverse) (SEQ ID NO:2). Amplified DNA was treated with Sph1 and HindIII restriction endonucleases, which were heat-inactivated after digestion. The fragment was ethanol-precipitated and combined with pETcoco-2 vector (Novagen) that had been treated with the same enzymes plus shrimp alkaline phosphatase. The fragments were ligated and the ligation mixture transformed into competent DH10 *E. coli*. Transformants were plated on F-medium plus glucose with 50 ug/ml ampicillin. Growth in glucose maintains the repressed state of the pBAD promoter driving expression of the replicator TrfA, thus maintaining low copy number. The resulting expression clone, pETcoco-Cdiff-MRS, was confirmed by sequencing of the insert in both directions.

Purification of *C. difficile* MetRS. The expression vector pETcoco-Cdiff-MRS was transformed into Rosetta DE3 expression strain and used to inoculate 4 liters of F media supplemented with 10 ug/mL chloramphenicol, 50 ug/mL ampicillin, 0.2% glucose. The culture was induced with 1 mM IPTG at OD 0.66. Cells were harvested 4 hours post-induction (yield=38 g cell pellet). Pelleted cells were lysed by adding 78 g of a 1:1 suspension of frozen cells (39 g cells) in Tris-sucrose which had been stored at −20° C. to 107.25 ml Tris-sucrose buffer that had been pre-warmed to 45° C. (2.75 ml/g of cells). To the stirred mixture, 1.95 ml of 0.5M 1,4-dithiothreitol (DTT) (0.05 ml/g of cells) and 9.75 ml of lysis buffer (2M NaCl, 0.3M spermidine in Tris-sucrose adjusted to pH 7.5) (0.25 ml/g of cells) was added. The pH of the slurry was tested with pH paper and adjusted to pH 8.0 by the addition of 50 ml of 2 M Tris base. Lysozyme (117 mg) was added in 20 ml of Tris-sucrose buffer (3 mg lysozyme/g of cells). The slurry was distributed into centrifuge bottles and incubated at 4° C. for 1 hour followed by incubation at 37° C. for 4 minutes. The insoluble cellular components were removed by centrifugation (23,000×g, 60 min, 4° C.). The recovered supernatant (192 ml) constituted Fraction I. Fraction I was loaded onto a 15 mL Ni-NTA column which was equilibrated in Load Buffer (50 mM Tris-HCl, pH 7.5, 10% glycerol, 40 mM KCl, 10 mM Imidazole, pH 6.8, and 7 mM beta mercaptoethanol). The column was washed with 10 column volumes of Wash Buffer (50 mM Tris-HCl, pH 7.5, 10% glycerol, 800 mM KCl, 20 mM Imidazole, pH 6.8, and 7 mM beta mercaptoethanol). The protein was eluted in 10 column volume gradient from Wash Buffer to Elution Buffer (50 mM Tris-HCl, pH 7.5, 10% glycerol, 40 mM KCl, 250 mM imidazole, pH 6.8, and 7 mM beta mercaptoethanol) at 0.5 mL/min collecting 3 mL fractions. Fractions were collected and analyzed for protein by SDS-PAGE. Fractions were assayed in the *C. difficile* MetRS tRNA charging assay. Fractions containing peak activity were pooled to form Fraction II (60 mg at 1.3 mg/ml). Fraction II had a specific activity of $3.2 \times 10^5$ units per mg. The purity was estimated at greater than 97% based on densitometry of an SDS-PAGE gel stained with Coomassie blue.

Example 14

Enantiomer Compounds are Potent Inhibitors of *C. difficile* MetRS

Compounds of the present invention were assayed to determine their ability to inhibit MetRS. Assays were performed as follows:

| Reaction Mix (per 1 ml) | | |
|---|---|---|
| Stock | Volume (µl) | Final Concentration |
| 100 mM Tris/Cl, pH 7.9 | 600 | 30 mM |
| 250 mM KCl | | 75 mM |
| 125 mM ATP | 40 | 2.5 mM |
| 250 mM MgCl$_2$ | 80 | 10 mM |
| 50 mM DTT | 80 | 2 mM |
| 1 mM Met (H-3 hot and cold) | 20 | 10 µM |
| Solid tRNA (Mixed *E. coli* MRE 600) | 4 mg/ml | 2 mg/ml |
| H$_2$O | 180 | |

10× Inhibitor (0-100 µM) 5 µl per well 0-10 µM

Each reaction was started by adding 20 µl appropriately diluted pure enzyme (pre-incubated with inhibitor) to 25 µl reaction mix for 10 min at room temperature. The reaction is terminated by the addition of 150 µl 167 mM sodium citrate, pH 2.15 containing phosphodiesterase (PDE) SPA beads (0.833 mg/ml). The binding of the radiolabelled product to the bead brings the isotope into close enough proximity to allow radiation from the tritium to excite the scintillant within the bead. Any unbound radiolabel is not close enough to the scintillant to allow this energy transfer, so no signal is generated. Following termination of the reaction, plates are spun at 2500 rpm for 5 min in a Mistral 3000E plate centrifuge (or alternatively allowed to stand for 1 hour). The assay is conducted in 96-well Optiplates (Packard). Plates are counted on a TopCount. (Packard 96 well counter).

Reagents

Mixed *E. coli* MRE 600 tRNA and ATP were purchased from Boehringer-Mannheim, L-[methyl-$^3$H]methionine and phosphodiesterase scintillation proximity (SPA) beads from Amersham Pharmacia Biotech and other reagents from Sigma.

Results

Pure enantiomers of the present invention (examples 2, 4, 6, 8, 10), all R enantiomers, and (example 11) S enantiomer, had very potent inhibition of *Clostridium difficile* MetRS in the range ($K_i$=15-25 pM). All were highly selective with respect to the mammalian enzyme (no inhibition of rat MetRS). Racemic mixtures of these examples had approximately 50% less activity than the pure enantiomers.

In comparison, the opposite configuration isomers (examples 3, 5, 7, 9), all S enantiomers, and (example 12) R enantiomer, had very weak inhibition of *Clostridium difficile* MetRS in the range ($K_i$=24,000-80,000 pM). This is an unanticipated dramatic difference in activity between isomers of opposite configuration. In addition, this data indicates that the compounds of the present invention show strong selectivity toward inhibition of *C. difficile* MetRS, but have little or no inhibitory activity toward mammalian MetRS. MetRS inhibitors are competitive inhibitors of methionine and uncompetitive inhibitors of ATP.

Example 15

Enantiomer Compounds have Potent Antibacterial Activity Against *C. difficile*

Compounds (formulas (VI)-(XI)) of the present invention were also assayed for their capacity to inhibit *C. difficile* growth. MIC$_{90}$ (minimum inhibition concentration required to inhibit the growth of 90% of *C. difficile*) was determined using standard agar based assays according to CLSI.

Organisms: All compounds were tested for antibacterial activity against a collection of non-repeat clinical isolates of *C. difficile*. The organisms were stored frozen in *Brucella* broth supplemented with 20% glycerol. The organisms were retrieved from the freezer and subcultured twice onto CDC agar to ensure purity and growth. The plates were incubated under anaerobic conditions for at least 24 hours. Bacterial colonies were examined for morphology; yellow color, ground glass texture and characteristic odor. The control organism tested was *Bacteroides fragilis* ATCC 25285.

Antimicrobial susceptibility testing: Antimicrobial susceptibility testing was conducted by the agar dilution method on *Brucella* agar supplemented with vitamin $K_1$, hemin and 5% laked sheep blood in accordance with CLSI guidelines (CLSI, M11-A2). The test compounds were serially diluted and added to molten supplemented *Brucella* agar. Drug free plates were inoculated before and after inoculation of each antimicrobial plate series and were used as growth controls. Anaerobic/aerobic growth controls were conducted on drug free plates after two sets of drug plates. Bacterial colonies were suspended in *Brucella* broth to a turbidity equal to that of a 0.5 McFarland standard and applied to a plate with a Steers replicator that delivered $10^5$ CFU/spot. The plates were incubated under anaerobic conditions for 24 hours at 35° C. prior to the reading of the results. The minimum inhibitory concentration (MIC) was the concentration that completely inhibited growth or caused a marked reduction in the appearance of growth compared to that of the drug-free growth control.

Results: Pure enantiomers of the present invention (examples 2, 4, 6, 8, 10), all R enantiomers, and (example 11) S enantiomer, had very potent antibacterial activity against *Clostridium difficile* ($MIC_{90}$=0.25 µg/ml to 4.0 µg/ml). Racemic mixtures of these examples had approximately 50% less activity than the pure enantiomers ($MIC_{90}$=0.50 µg/ml to 8.0 µg/ml).

In comparison, the opposite configuration isomers (examples 3, 5, 7, 9), all S enantiomers, and (example 12) R enantiomer, had very weak antibacterial activity against *Clostridium difficile* ($MIC_{90}$=>8.0 µg/ml to >32.0 µg/ml).

These results indicate the potent activity of the pure enantiomeric compounds of the present invention against *C. difficile*, typically around 0.25-1.0 µg/ml. In addition, $IC_{50}$ data indicates that the compounds of the present invention are specific for *C. difficile* MetRS, showing little or no activity against mammalian MetRS. MetRS inhibitor compounds show potent activity against *C. difficile* and gram positive bacteria while sparing normal gut flora.

The data in these examples illustrate the potent and unexpected antibacterial effectiveness of the pure R enantiomers in the case of examples 2, 4, 6, 8, 10 and the S enantiomer example 11 as compared to the very weak activity of their opposite configuration isomers (examples 3, 5, 7, 9, 12).

Example 16

Compounds of the Present Invention have Potent Antibacterial Activity Against Other Bacteria Compounds of the present invention (examples 2, 4, 6, 8, 10, and 11) were tested for antibacterial activity against a panel of Gram-positive bacteria. Compounds were tested against Gram-positive aerobic bacteria using the CLSI-reference broth microdilution method. Data was obtained against *S. aureus, E. faecalis, E. faecium, S. pyogenes, S. epidermidis* and *S. haemolyticus*. The compounds tested demonstrated potent antibacterial activity against all isolates with a MIC range of <0.008-8 µg/ml, including resistant strains of *S. aureus, S. epidennidis* and *S. pyogenes*. Data was also obtained against *Helicobacter, H. pylori* using the standard CLSI guideline agar dilution method and results indicate that the compounds of the invention are active against *H. pylori*.

The data illustrated the utility of using the compounds of the present invention as antibacterial agents against other Gram-positive bacteria, e.g., *S. aureus, E. faecalis, E. faecium S. pyogenes, S. epidennidis*, and *S. haemolyticus* and against the Gram-negative bacteria *H. pylori*.

Example 17

Compounds of the Present Invention Show Strong Therapeutic Utility During In Vivo Trials Animal studies were performed to determine the efficacy of MetRS inhibitors for treating *C. difficile*-infections. The MetRS inhibitors tested were 5-[3-((R)-6,8-Dibromo-chroman-4-ylamino)-propylamino]-4H-thieno[3,2-b]pyridine-7-one (both racemic mixture and the R enantiomer) and 5-[3-((R)-8-Bromo-6-chloro-chroman-4-ylamino)-propylamino]-4H-thieno[3,2-b]pyridin-7-one. Also tested was 2-(3-{3,5-Dibromo-2-[2-(4-methyl-thiazol-5-yl)-ethoxy]-benzylamino}-propylamino)-1H-quinolin-4-one.

Results were compared to *C. difficile*-infected hamsters treated with the conventional antibiotic, vancomycin. Infected hamsters were treated with either a solution or suspension of a MetRS inhibitor at 5 to 50 mg/kg or vancomycin at 2.5, 5 or 25 mg/kg. There were eight hamsters per group with the final endpoint of the experiment being survival. Expired hamsters were examined for GI condition.

Data for the studies indicated that control hamsters (infected with *C. difficile* but receiving no treatment) died within 3-4 days. Hamsters treated with MetRS inhibitors showed a significant increase in survival, often living until study termination, typically 28 or more days. These results were similar or superior to the results obtained using vancomycin treatment. 5-[3-((R)-6,8-Dibromo-chroman-4-ylamino)-propylamino]-4H-thieno[3,2-b]pyridine-7-one demonstrated the best efficacy. 5-[3-((R)-6,8-Dibromo-chroman-4-ylamino)-propylamino]-4H-thieno[3,2-b]pyridine-7-one exhibited superior efficacy to vancomycin in that >60% survival was observed on Day 28 (5 mg/kg BID) as compared to 0-10% survival with vancomycin. Surviving animals had healthy GI appearance and histopathology. Low systemic exposure and bioavailability was observed in hamsters following oral administration of the MetRS inhibitors.

The data in this Example illustrates that the compounds of the present invention were comparable or superior to vancomycin in their capability to treat animals infected with *C. difficile*.

Example 18

Compounds of the Present Invention Effect Toxin Production in *C. difficile*

The pathogenicity of *C. difficile* is associated with its ability to produce the extracellular toxins A and B. Hypertoxinogenic strains are responsible for recent outbreaks with high mortality. In contrast, isolates that do not produce toxins are non-pathogenic. Since toxin production requires active protein synthesis, inhibition of the protein synthesis machinery is expected to suppress de novo toxin production. Therefore, MetRS inhibitors were evaluated for their effect on *C. difficile* toxin production in vitro.

Methods:

C. difficile strain ATCC43255 was grown and maintained anaerobically on CDC anaerobe agar (Remel, Lenexa, Kans.). To test the effect of antibacterial agents on growth, cells were grown anaerobically for 40 h at 35° C. in 96-well brain heart infusion (BHI) broth cultures, with an initial inoculum of $10^6$ CFU/mL. To test the effect of antibacterial agents on toxin production at high C. difficile cell densities, the cells were grown anaerobically for 24 h at 35° C. in 96-well brain heart infusion (BHI) broth cultures. Spent medium was then replaced with fresh broth containing MetRS inhibitors and control agents at a concentration range of 0.015-16 µg/mL. After 4 days, growth and cell viability were monitored by optical density measurements at 595 nm and by culture on CDC anaerobe agar, respectively. Culture supernatants were collected, and toxin A was detected by ELIFA (enzyme-linked immuno-flow assay) using an anti toxin A monoclonal antibody (Novus Biologicals, Centennial, Colo.).

Results:

The MetRS inhibitors 5-[3-(6,8-Dibromo-chroman-4-ylamino)-propylamino]-4H-thieno[3,2-b]pyridin-7-one and 5-(3-{3,5-Dibromo-2-[2-(4-methyl-thiazol-5-yl)-ethoxy]-benzylamino}-propylamino)-4H-thieno[3,2-b]pyridin-7-one prevented growth of C. difficile in broth at concentrations of $\geq 0.25$ µg/mL.

Toxin production in high cell density, 4 day old stationary phase cultures was inhibited by four different MetRS inhibitors (5-[3-(6,8-Dibromo-chroman-4-ylamino)-propylamino]-4H-thieno[3,2-b]pyridin-7-one, 5-(3-{3,5-Dibromo-2-[2-(4-methyl-thiazol-5-yl)-ethoxy]-benzylamino}-propylamino)-4H-thieno[3,2-b]pyridin-7-one, R-(+)-5-[3-(6,8-Dibromo-chroman-4-ylamino)-propylamino]-4H-thieno[3,2-b]pyridin-7-one di-hydrochloride, 5-[3-(6,8-Dibromo-1,2,3,4-tetrahydro-quinolin-4-ylamino)-propylamino]-4H-thieno[3,2-b]pyridin-7-one tri-hydrochloride) at concentrations as low as 0.25 µg/mL. In contrast, much higher concentrations (4->16 µg/mL) of the comparator agents (metronidazole, vancomycin, levofloxacin) were required to inhibit toxin production.

Conclusions:

MetRS inhibitors demonstrate inhibitory effects on both growth and toxin production of C. difficile in broth cultures. Furthermore, toxin production was effectively blocked in stationary phase cultures. As a consequence of this suppression of toxin production by bacteriostatic MetRS inhibitors, C. difficile becomes essentially non-toxinogenic and thus non-pathogenic. This effect is unique to protein synthesis inhibitors, such as MetRS inhibitors, whose mode-of-action does not require that the bacteria are actively growing.

Example 19

Compounds of the Present Invention Effect Spore Production in C. difficile

C. difficile is an organism well known for its ability to form spores that are resistant to heating, drying and many cleaning agents such as disinfectants. Spores present in the environment may serve as a reservoir for disease-causing organisms. C. difficile infections are often initiated by the ingestion of spores that germinate in the GI tract causing CDAD. Spore retention in the gut after treatment for CDAD is also thought to be a major source of relapsing disease. Reduction in the capacity of C. difficile to produce spores or spore germination could represent an important breakthrough in the treatment of this disease. Spore coats are composed primarily of protein, generation of the spore coat requires protein synthesis and inhibition of active protein synthesis is expected to affect spore production in this organism. Therefore, MetRS inhibitors were evaluated for their effect on C. difficile spore production in vitro.

Methods:

MetRS inhibitors were evaluated for their effect on sporulation of four clinical isolates of C. difficile, including two recent outbreak isolates that belong to the BI/NAP1 genotype. C. difficile strains were grown on supplemented Brucella blood for 24 to 48 hours and colonies suspended in saline to achieve a turbidity equivalent to a 0.5 McFarland standard. C. difficile suspensions (10 µL) were spread onto the surface of fresh supplemented Brucella agar plates with 5% laked sheep blood containing MetRS inhibitors at concentrations ranging from 0.06 to 2 µg/mL and incubated anaerobically at 35° C. for 96 hours. Aliquots of the same cell suspensions used to inoculate the MetRS containing plates were also plated for viable counts and an additional 250 µL aliquot was treated with 250 µL of absolute ethanol for 1 hour at room temperature to eliminate vegetative cells and permit the enumeration of spores. The ratio of spores to total cells was again determined for all four strains after 96 hours of incubation in the presence of compound and used to compare the effects of MetRS inhibitors with drug free controls on sporulation rates.

Results:

Three out of four C. difficile strains produced measurable number of spores and were evaluated as described above. Treatment of all strains with 5-[3-((R)-6,8-Dibromo-chroman-4-ylamino)-propylamino]-4H-thieno[3,2-b]pyridine-7-one (Formula IX, Example 2) in all strains showed reductions in spore production at 0.25×MIC (<2% spores) and at 0.5× MIC (<1% spores). This is in marked contrast to the results obtained after treatment with metronidazole, where all tested strains display marked increases in spore production (up to 100% spores) after exposure to subMIC concentrations of the drug. Treatment with vancomycin induced similar spore production increases in two strains but not in one strain where the spore counts remained low.

Conclusions:

5-[3-((R)-6,8-Dibromo-chroman-4-ylamino)-propylamino]-4H-thieno[3,2-b]pyridin-7-one at subMIC (0.25 and 0.5×MIC) was effective in preventing vegetative cells of C. difficile from forming spores. These data suggest that 5-[3-((R)-6,8-Dibromo-chroman-4-ylamino)-propylamino]-4H-thieno[3,2-b]pyridin-7-one might also have a useful role in preventing outbreaks and reducing relapse rates that have been correlated with widespread prevalence of C. difficile spores in the environment.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. An optically active compound of the formula (IIa) or (IIb):

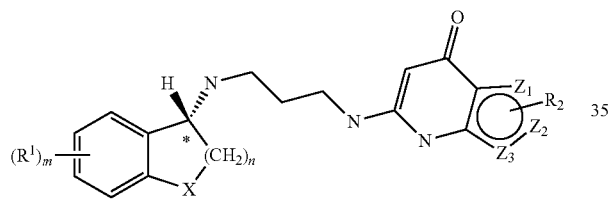

in which:
X is selected from the group consisting of NH, O, S, SO, $SO_2$, or $CH_2$;
n is 1, 2 or 3;
* indicates an asymmetric carbon atom, wherein when n is 2 or 3, then * is R configuration; wherein when n is 1 and X is $CH_2$, then * is R configuration; and wherein when n is 1 and X is selected from the group consisting of NH, O, S, SO, or $SO_2$, then * is S configuration;
$R^1$ is independently selected from halo, cyano, hydroxyl, $(C_{1-6})$alkyl (optionally substituted by halo, hydroxyl, amino, carboxy, or $(C_{1-6})$alkoxycarbonyl), $(C_{3-7})$cycloalkyl, $C_{(1-6)}$alkoxy, amino, mono- or di-$(C_{1-6})$alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl and heterocyclic;
m is 0, 1, 2, 3 or 4;
$R^2$ is independently selected from halo, cyano, hydroxyl, $(C_{1-6})$alkyl (optionally substituted by halo, hydroxyl, amino, carboxy, or $(C_{1-6})$alkoxycarbonyl), $(C_{3-7})$cycloalkyl, $C_{(1-6)}$alkoxy, amino, mono- or di-$(C_{1-6})$alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl and heterocyclic; and when $Z_1$ is S, $Z_2$ and $Z_3$ are CH; when $Z_2$ is S, $Z_1$ and $Z_3$ are CH; and when $Z_3$ is S, $Z_1$ and $Z_2$ are CH.

2. An optically active compound of claim 1 having the formula (III):

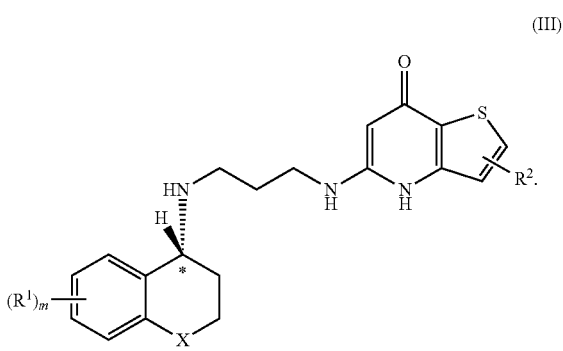

3. The optically active compound of claim 2 wherein $(R^1)_m$ is a 6, 8 substitution and can be the same or different substituents, wherein the substituents are selected from the group consisting of bromine, chlorine, iodine and sulfane.

4. An active compound of claim 1 having a formula (V):

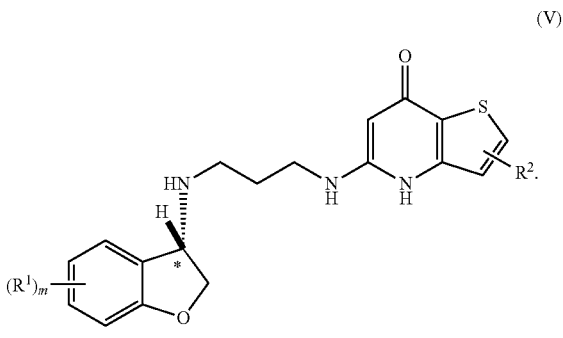

5. The optically active compound of claim 4 wherein $(R^1)_m$ is a 5, 7 substitution and can be the same or different substituents, wherein the substituents are selected from the group consisting of bromine, chlorine, iodine and sulfane.

6. An optically active compound of claim 1 selected from the group consisting of:

- 5-[3-((R)(−)-5,7-Dibromo-1,2,3,4-tetrahydro-naphthalen-1-ylamino)-propylamino]-4H-thieno[3,2-b]pyridine-7-one;
- 5-[3-((R)(+)-8-Bromo-6-chloro-chroman-4-ylamino)-propylamino]-4H-thieno[3,2-b]pyridine-7-one;
- 5-[3-((R)(+)-6,8-Dibromo-1,2,3,4-tetrahydro-quinolin-4-ylamino)-propylamino]-4H-thieno[3,2-b]pyridine-7-one;
- 5-[3-((R)(+)-6,8-Dibromo-chroman-4-ylamino)-propylamino]-4H-thieno[3,2-b]pyridine-7-one; and
- 5-[3-((S)-5,7-Dibromo-benzofuran-3-ylamino)-propylamino]-4H-thieno[3,2-b]pyridine-7-one.

7. The salt of the compound of claim 1, wherein the salt is a pharmaceutically acceptable salt.

8. A compound as in claim 1 for use in the treatment of Gram-positive bacterial infections.

9. A pharmaceutical composition for the treatment of a Gram-positive bacterial infection in a human, comprising a compound of claim 1 in an effective amount so as to reduce the growth of said bacteria, the preparation further comprising a pharmaceutically acceptable carrier or excipient.

* * * * *